(12) United States Patent
Houghton et al.

(10) Patent No.: US 7,695,925 B2
(45) Date of Patent: Apr. 13, 2010

(54) **COMPOSITIONS AND METHODS FOR THE DETECTION OF *TRYPANOSOMA CRUZI* INFECTION**

(75) Inventors: Raymond L. Houghton, Seattle, WA (US); Steven G. Reed, Seattle, WA (US); Syamal Raychaudhuri, Seattle, WA (US)

(73) Assignees: Inbios International, Inc., Seattle, WA (US); Infectious Disease Research Institute, Seattle, WA (US)

( * ) Notice: Subject to any disclaimer, the term of this patent is extended or adjusted under 35 U.S.C. 154(b) by 0 days.

(21) Appl. No.: 12/092,562

(22) PCT Filed: Nov. 2, 2006

(86) PCT No.: PCT/US2006/042907
§ 371 (c)(1),
(2), (4) Date: May 2, 2008

(87) PCT Pub. No.: WO2007/056114
PCT Pub. Date: May 18, 2007

(65) Prior Publication Data
US 2008/0287362 A1    Nov. 20, 2008

Related U.S. Application Data

(60) Provisional application No. 60/733,119, filed on Nov. 3, 2005.

(51) Int. Cl.
*G01N 33/53*    (2006.01)

(52) U.S. Cl. .................... 435/7.22; 435/7.1; 435/7.72; 435/975; 424/269.1; 424/185.1; 424/192.1; 530/350

(58) Field of Classification Search ............... None
See application file for complete search history.

(56) References Cited

U.S. PATENT DOCUMENTS

| | | |
|---|---|---|
| 5,876,734 A | 3/1999 | Kirchhoff et al. |
| 6,228,372 B1 | 5/2001 | Reed et al. |
| 6,228,601 B1 | 5/2001 | Kirchhoff et al. |
| 6,419,933 B1 | 7/2002 | Reed et al. |
| 6,458,922 B1 | 10/2002 | Zrein |
| 2004/0132077 A1 | 7/2004 | Kirchhoff et al. |

OTHER PUBLICATIONS

Mikayama et al. (Nov. 1993. Proc.Natl.Acad.Sci. USA, vol. 90: 10056-10060).*
Rudinger et al. (Jun. 1976. Peptide Hormones. Biol.Council. pp. 5-7).*
Greenspan et al (Nature Biotechnology 7: 936-937, 1999.*
Chothia et al (The EMBO Journal, 1986, 5/4:823-26).*
Ferreira, A.W., et al., "Enzyme-Linked Immunosorbent Assay for Serological Diagnosis of Chagas' Disease Employing a *Trypanosoma cruzi* Recombinant Antigen That Consists of Four Different Peptides," Journal of Clinical Microbiology, vol. 39, No. 12, pp. 4390-4395 (Dec. 2001).
Houghton, Raymond L., et al., "A Multi-Epitope Synthetic Peptide and Recombinant Protein for the Detection of Antibodies to *Trypanosoma cruzi* in Radioimmunoprecipitation-Confirmed and Consensus-Positive Sera," The Journal of Infectious Diseases, vol. 179, pp. 1226-1234 (May 1999).
Cardinal, Maria V., et al., "Use of an Immunochromatographic Dipstick Test for Rapid Detection of *Trypanosoma cruzi* in Sera from Animal Reservoir Hosts," Journal of Clinical Microbiology, vol. 44, No. 8, pp. 3005-3007 (Aug. 2006).
Thomas, M.C., et al., "Mapping of the antigenic determinants of the *T. cruzi* kinetoplastid membrane protein-11. Identification of a linear epitope specifically recognized by human Chagasic sera," Clinical & Experimental Immunology, vol. 123, pp. 465-471 (2001).

* cited by examiner

*Primary Examiner*—Jennifer E Graser
(74) *Attorney, Agent, or Firm*—Janet Sleath; Speckman Law Group PLLC

(57) ABSTRACT

Compositions comprising fusion polypeptides of *T. cruzi* epitopes are provided, together with methods for the use of such compositions in the diagnosis of *T. cruzi* infection and in screening blood supplies. Diagnostic kits comprising such compositions are also provided.

16 Claims, 6 Drawing Sheets

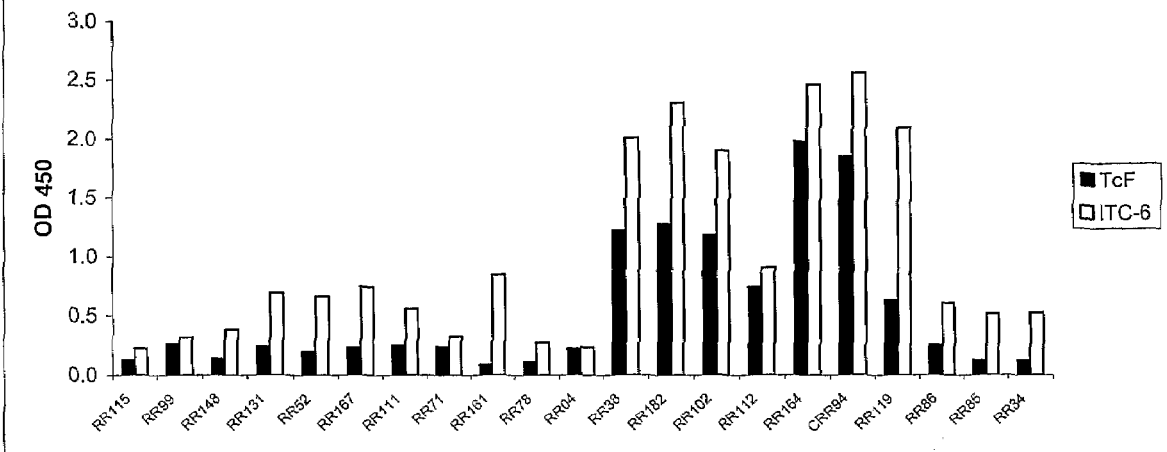
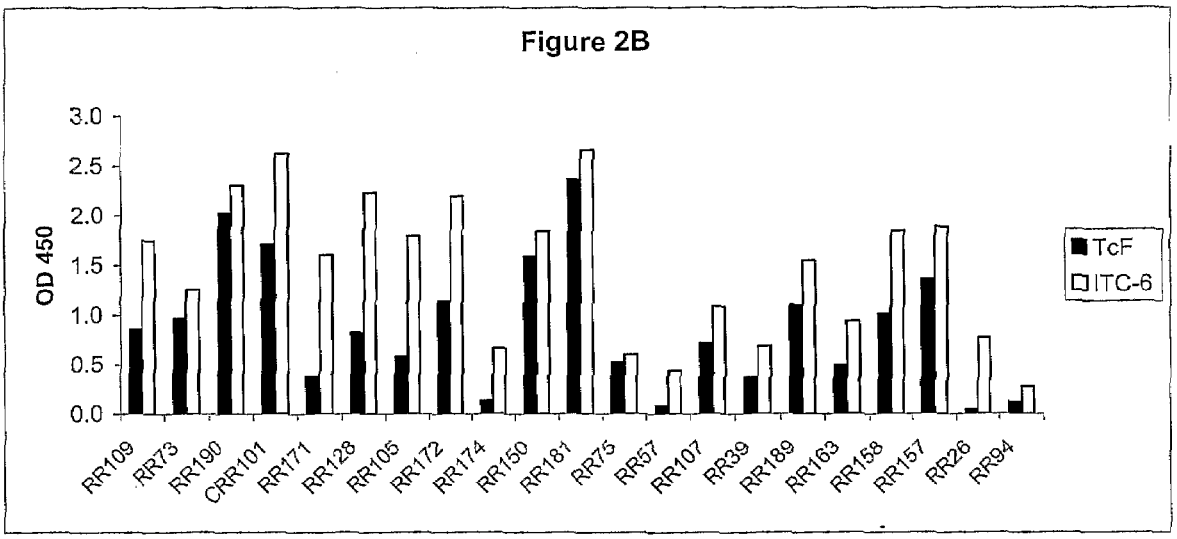
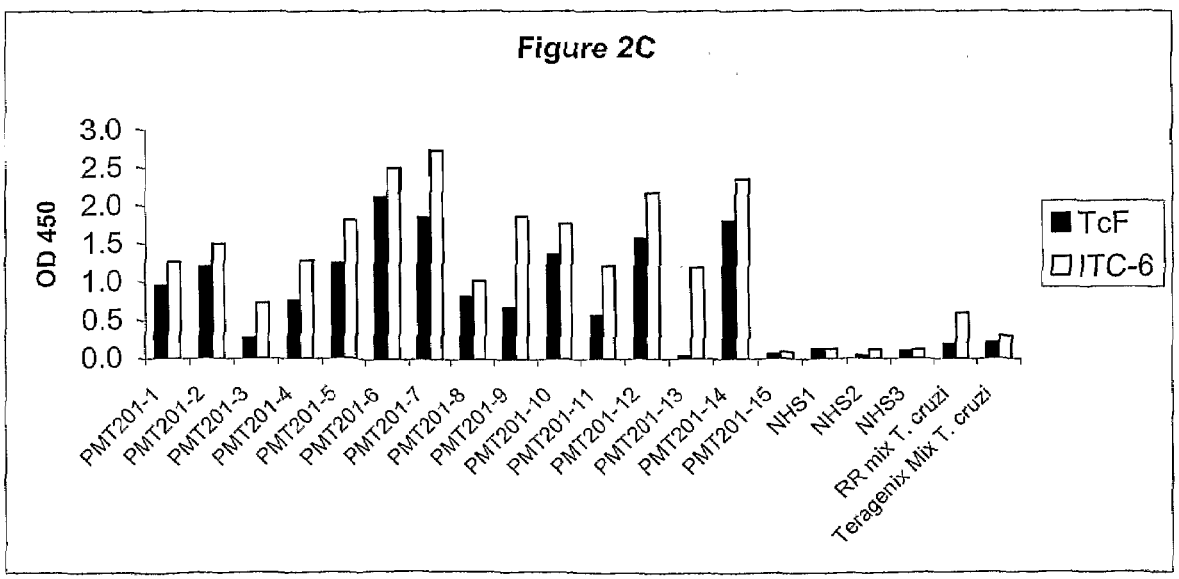

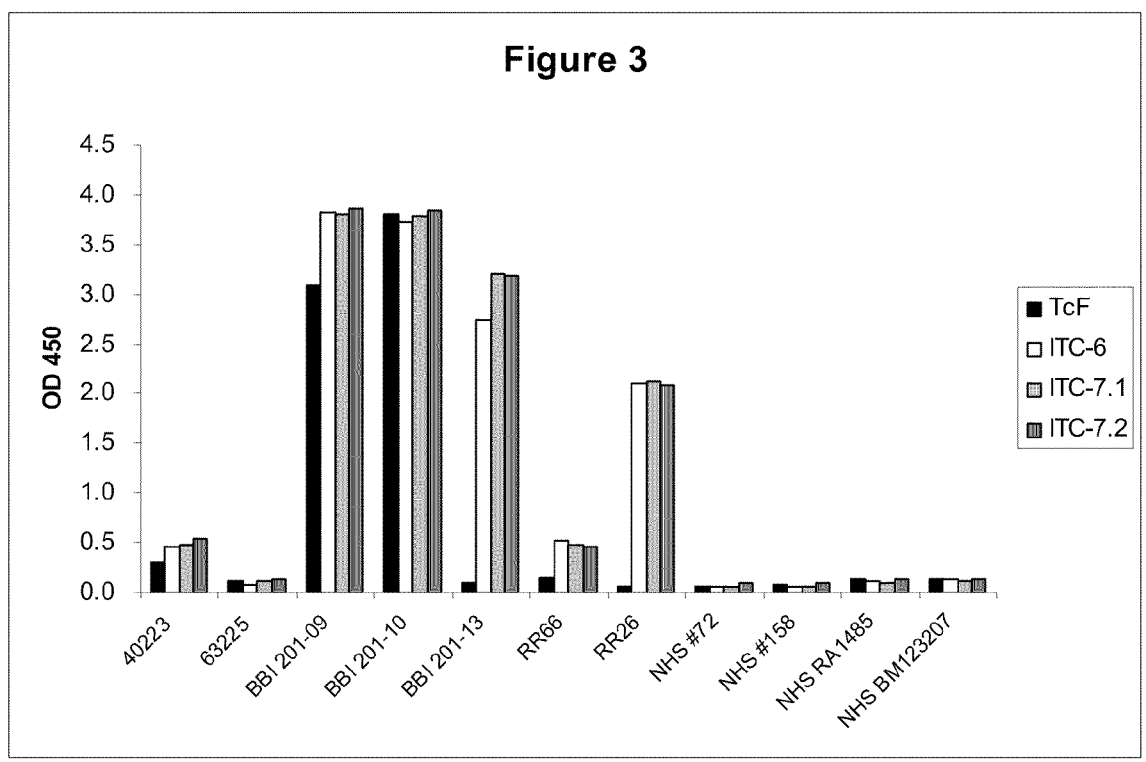

Figure 6A

ATGGGCAGCAGCCATCATCATCATCATCACAGCAGCGGCCTGGTGCCGCG
CGGCAGCCATATGGCCGCAGGCGGAGAGCTGGCGGCAACAGCAGCTG
CAGTGCGGGGACAGTTTGCA<u>T</u>CGTGTGCCCGTGGGGGAAGGACGAC
ATGGCGCAGGATGGGCTTCTGGAG<u>G</u>CTGAGCTTTTCACCCCGGTGGA
TGAGAGCCTCTAGTCCAGCAGACGTGCTGAGCATGGGGAGAAGGAGC
TGTGACCGCCCCGTATTTTGGCCTCAGAGCCAGAGTGCACCCTGTCG
AAGGCAAAAAGGGGCGAAGTCGACACAATGC<u>G</u>ACTTGTCCACGAAGC
GCTTCTTCCTCCCATGCTCTGGCAGAGGCGTGCCGGGAGGATACTGC
GAACAGTTGCGCTTTGTTGTTGGCTGTGGTGGCGGGGAGGGCGGAG
GGGCAGACTCAACTGAAAGCTT

<u>T</u>    This is 'A' in XM803645
<u>G</u>    This is 'A' in XM803645
<u>G</u>    This is 'C' in XM803645

Figure 6B

MGSSHHHHHHSSGLVPRGSHMAAGGELAATAAAVRGQFASCARGGRTT
WRRMGFWRLSFSPRWMRASSPADVLSMGRRSCDRPVFWPQSQSAPCRR
QKGAKSTQCDLSTKRFFLPCSGRGVPGGYCEQLRFCCWLWWRGGRRG
RLN*

Figure 7A

ATGGGCAGCAGCCATCATCATCATCATCACAGCAGCGGCCTGGTGCCGCG
CGGCAGCCATATGCCCAAAAAGACCGGTGGCAAAAAGAAGGGGCAAA
GTTCTCCGGATGGCTCTGAGCCGCGGAAACGAAGAACAACAAAAAG
GCGACAATGGAGCCGCGGGACGTGGATGAGATGCAGAAGCTGCAGG
AACTTTTAGGGGACGAGGAACAGCCGTTGGGTGTCTCCAAGAAATCG
CTAGAGGGCTTATTGTCCCTTCGGCAGCCGCAGGAGTTGGCGGTGAG
GCTTGCGCAATCTCTCTCCTCCCTGCGCGCGCGGCTTGCGGAGTTGG
AGTTGGAGAGGCTTAACCGTGGGAGCGAGGCGCCGGGGCTGTCGAA
CATCGT...

Figure 7B

MGSSHHHHHHSSGLVPRGSHMPKKTGGKKKGQSSPDGSEPRKRKNNKKA
TMEPRDVDEMQKLQELLGDEEQPLGVSKKSLEGLLSLRQPQELAVRLA
QSLSSLRARLAELELERLNRGSEAPGLSNI...

Figure 8A

CCATGGGCAGCAGCCATCATCATCATCATCACAGCAGCGGCCTGGTGCCG
CGCGGCAGCCATATGTGCATTGCTCTTGGCATCGTCGCGGAGGATGAT
GAGGCATGGCGAATTGCCAGCGAGGCTGTCGCTGCAGAAAGGAGC
CTGTCTTCAGCGGGAACAACGGCCCTTTTGTAGATGTCTGGTTTGGC
GAACAGAAACTCTTTGGCCTCGTTAACGCGTTGCTCCAAACGACTTT
ATTCAGGTCGCCCAGGAGTGTGGCGAGAAGAGCGATGACGCCGCAG
CGACGTTGCGGATGCGTGTGACGCACAACGTCTCTTTGTCCTTCACC
TCTCGTCGGTGCCGCATGCGATGCTGCAGGCACGGGGAGCGCCCGA
GGACAAGTTTGTGAACTTCATGCAACTTGTCGTGGATTACGCTTCGCT
GCTGCGGCGCGGGATGAAGGATGAGTTTCTTGGCGTCGATCCCGAGT
CCGATGCGGAGTACATACGCTTCACGCCCAGTGAAGCTT

Figure 8B

MGSSHHHHHHSSGLVPRGSHMCIALGIVAEDDEAWRIASEAVAAEKEPVFS
GNNGPFVDVWFGEQKLFGLVQRVAPNDFIQVAQECGEKSDDAAATLRM
RVTHNVSFVLHLSSVPHAMLQARGAPEDKFVNFMQLVVDYASLLRRGM
KDEFLGVDPESDAEYIRFTPQ*

Figure 9A

CCATGGGCAGCAGCCATCATCATCATCATCACAGCAGCGGCCTGGTGCCG
CGCGGCAGCCATATGTGTTCCAATACGGACCCTTGAGGAACTCATCG
CAGCGTGGAAGACCGATCGCTGTGTCTGTTGCCAACTCGTGTCTTCG
CGTAGCGGCCACGCAGAAAGTTTCTAAGCCACCTTCTACAGTTCACC
CCCGGAATATTGGCCGGCAAGCGACTGAGGACTCGATGACCAATGAA
CTCAAAGGCCTTGCTGGAGTCTACCAGCACCAACGGAGCCCGATGGG
GTCTGCAGTGGAGCTGGCTTCCAACACCGCTCTTCCTGGGAAGGTTC
ACTTGGAATTAATCGTTTCTGTTATGCTCAAATTCGTTTATCAGGTGT
GCCAGCTGCATCGTCGTGGTACGCATACTACGGCACGCATACTGGTG
CGGACGAGGCGTCCACAGCCAAAGCAGTCTCCTCAATGCCATTTTCT
CAGCAACCTTACCCACGATGGAAGGACAGCTGATTGGTCGATATGAA
GCTT

Figure 9B

MGSSHHHHHHSSGLVPRGSHMCSQYGPLRNSSQRGRPIAVSVANSCLRVA
ATQKVSKPPSTVHPRNIGRQATEDSMTNELKGLAGVYQHQRSPMGSAVE
LASNTALPGKVHLELIVSVMLKFVYQVCQLHRRGTHTTARILVRTRRPQ
PKQSPQCHFLSNLTHDGRTADWSI*

SEQUENCE LISTING

```
<160> NUMBER OF SEQ ID NOS: 31

<210> SEQ ID NO 1
<211> LENGTH: 78
<212> TYPE: PRT
<213> ORGANISM: T. Cruzi

<400> SEQUENCE: 1

Gly Asp Lys Pro Ser Pro Phe Gly Gln Ala Ala Ala Gly Asp Lys Pro
1               5                   10                  15

Ser Pro Phe Gly Gln Ala Ala Glu Pro Lys Ser Ala Glu Pro Lys Pro
            20                  25                  30

Ala Glu Pro Lys Ser Lys Ala Ala Ile Ala Pro Ala Lys Ala Ala Ala
        35                  40                  45

Ala Pro Ala Lys Ala Ala Thr Ala Pro Ala Ser Ser Met Pro Ser Gly
    50                  55                  60

Thr Ser Glu Glu Gly Ser Arg Gly Gly Ser Ser Met Pro Ala
65                  70                  75

<210> SEQ ID NO 2
```

```
<211> LENGTH: 25
<212> TYPE: PRT
<213> ORGANISM: T. Cruzi

<400> SEQUENCE: 2

Tyr Asp Ser Thr Ala His Gly Thr Pro Ser Thr Pro Ala Asp Ser Ser
 1               5                  10                  15

Ala His Ser Thr Pro Ser Thr Pro Ala
            20                  25

<210> SEQ ID NO 3
<211> LENGTH: 29
<212> TYPE: PRT
<213> ORGANISM: T. Cruzi

<400> SEQUENCE: 3

Tyr Glu Lys Gln Lys Ala Ala Glu Ala Thr Lys Val Ala Glu Ala Glu
 1               5                  10                  15

Lys Gln Arg Ala Ala Glu Ala Thr Lys Val Ala Glu Ala
            20                  25

<210> SEQ ID NO 4
<211> LENGTH: 38
<212> TYPE: PRT
<213> ORGANISM: T. Cruzi

<400> SEQUENCE: 4

Ala Leu Pro Gln Glu Glu Gln Glu Asp Val Gly Pro Arg His Val Asp
 1               5                  10                  15

Pro Asp His Phe Arg Ser Thr Thr Gln Asp Ala Tyr Arg Pro Val Asp
            20                  25                  30

Pro Ser Ala Tyr Lys Arg
            35

<210> SEQ ID NO 5
<211> LENGTH: 17
<212> TYPE: PRT
<213> ORGANISM: T. Cruzi

<400> SEQUENCE: 5

Lys Phe Ala Glu Leu Leu Glu Gln Gln Lys Asn Ala Gln Phe Pro Gly
 1               5                  10                  15

Lys

<210> SEQ ID NO 6
<211> LENGTH: 68
<212> TYPE: PRT
<213> ORGANISM: T. Cruzi

<400> SEQUENCE: 6

Met Glu Gln Glu Arg Arg Gln Leu Leu Glu Lys Asp Pro Arg Arg Asn
 1               5                  10                  15

Ala Lys Glu Ile Ala Ala Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Arg Val Pro Leu Ala Asp Val Pro Leu Asp Asp Asp Ser
    50                  55                  60

Asp Phe Val Ala
65
```

```
<210> SEQ ID NO 7
<211> LENGTH: 60
<212> TYPE: PRT
<213> ORGANISM: T. Cruzi

<400> SEQUENCE: 7

Arg Ala Gln Glu Leu Ala Arg Glu Lys Lys Leu Ala Asp Arg Ala Phe
 1               5                  10                  15

Leu Asp Gln Lys Pro Glu Arg Val Pro Leu Ala Asp Val Pro Leu Asp
            20                  25                  30

Asp Asp Ser Asp Phe Val Ala Met Glu Gln Glu Arg Arg Gln Leu Leu
        35                  40                  45

Glu Lys Asp Pro Arg Arg Asn Ala Lys Glu Ile Ala
    50                  55                  60

<210> SEQ ID NO 8
<211> LENGTH: 174
<212> TYPE: PRT
<213> ORGANISM: T. Cruzi

<400> SEQUENCE: 8

Gly Asp Lys Pro Ser Pro Phe Gly Gln Ala Ala Ala Gly Asp Lys Pro
 1               5                  10                  15

Ser Pro Phe Gly Gln Ala Ala Glu Pro Lys Ser Ala Glu Pro Lys Pro
            20                  25                  30

Ala Glu Pro Lys Ser Lys Ala Ala Ile Ala Pro Ala Lys Ala Ala
        35                  40                  45

Ala Pro Ala Lys Ala Ala Thr Ala Pro Ala Ser Ser Met Pro Ser Gly
    50                  55                  60

Thr Ser Glu Glu Gly Ser Arg Gly Gly Ser Ser Met Pro Ala Glu Phe
65                  70                  75                  80

Tyr Asp Ser Thr Ala His Gly Thr Pro Ser Thr Pro Ala Asp Ser Ser
                85                  90                  95

Ala His Ser Thr Pro Ser Thr Pro Ala Tyr Glu Lys Gln Lys Ala Ala
            100                 105                 110

Glu Ala Thr Lys Val Ala Glu Ala Glu Lys Gln Arg Ala Ala Glu Ala
        115                 120                 125

Thr Lys Val Ala Glu Ala Ala Leu Pro Gln Glu Gln Glu Asp Val
    130                 135                 140

Gly Pro Arg His Val Asp Pro Asp His Phe Arg Ser Thr Thr Gln Asp
145                 150                 155                 160

Ala Tyr Arg Pro Val Asp Pro Ser Ala Tyr Lys Arg Lys Leu
                165                 170

<210> SEQ ID NO 9
<211> LENGTH: 92
<212> TYPE: PRT
<213> ORGANISM: T. Cruzi

<400> SEQUENCE: 9

Tyr Asp Ser Thr Ala His Gly Thr Pro Ser Thr Pro Ala Asp Ser Ser
 1               5                  10                  15

Ala His Ser Thr Pro Ser Thr Pro Ala Tyr Glu Lys Gln Lys Ala Ala
            20                  25                  30

Glu Ala Thr Lys Val Ala Glu Ala Glu Lys Gln Arg Ala Ala Glu Ala
        35                  40                  45

Thr Lys Val Ala Glu Ala Ala Leu Pro Gln Glu Gln Glu Asp Val
```

```
            50                  55                  60
Gly Pro Arg His Val Asp Pro Asp His Phe Arg Ser Thr Thr Gln Asp
 65                  70                  75                  80

Ala Tyr Arg Pro Val Asp Pro Ser Ala Tyr Lys Arg
                 85                  90

<210> SEQ ID NO 10
<211> LENGTH: 297
<212> TYPE: DNA
<213> ORGANISM: T. Cruzi

<400> SEQUENCE: 10
gaattctatg attccaccgc ccatggtacc cctagcaccc ccgccgattc ctccgcccat    60
tccaccccat ccaccccagc ctatgaaaaa caaaaagccg ccgaagccac caaagtagca   120
gaagccgaaa acaacgtgc cgcagaagcc accaaagtag ccgaagccgc cctcccccaa    180
gaagaacaag aagatgtcgg tccccgccat gtagatccag accactttcg ctccaccaca   240
caagatgcct accgcccagt tgacccctcc gcctataaac gtaagctttg actcgag      297

<210> SEQ ID NO 11
<211> LENGTH: 525
<212> TYPE: DNA
<213> ORGANISM: T. Cruzi

<400> SEQUENCE: 11
ggtgataagc ctagcccatt tggtcaggct gctgctggtg acaaaccgtc tccgttcggt    60
caggctgctg aaccgaaatc tgctgaaccg aaaccggctg aaccgaaaag caaagctgct   120
atcgctccgg ctaaagctgc tgctgctccg gctaaagctg ctaccgctcc ggcctcttct   180
atgccgtctg gtacctctga agaaggttct cgtggtggtt cttctatgcc ggccgaattc   240
tatgattcca ccgcccatgg taccctagc accccgccg attcctccgc ccattccacc    300
ccatccaccc cagcctatga aaacaaaaa gccgccgaag ccaccaaagt agcagaagcc   360 gaaaacaac gtgccgcaga agccaccaaa gtagccgaag ccgccctccc ccaagaagaa   420
caagaagatg tcggtccccg ccatgtagat ccagaccact ttcgctccac cacacaagat   480
gcctaccgcc cagttgaccc ctccgcctat aaacgtaagc tttga                   525

<210> SEQ ID NO 12
<211> LENGTH: 33
<212> TYPE: DNA
<213> ORGANISM: Artificial Sequence
<220> FEATURE:
<223> OTHER INFORMATION: Made in a lab

<400> SEQUENCE: 12
caattacata tgtatgattc caccgcccat ggt                                 33

<210> SEQ ID NO 13
<211> LENGTH: 33
<212> TYPE: DNA
<213> ORGANISM: Artificial Sequence
<220> FEATURE:
<223> OTHER INFORMATION: Made in a lab

<400> SEQUENCE: 13
caattactcg agtcaaagct tacgtttata ggc                                 33

<210> SEQ ID NO 14
<211> LENGTH: 594
```

<212> TYPE: DNA
<213> ORGANISM: Artificial Sequence
<220> FEATURE:
<223> OTHER INFORMATION: Made in a lab

<400> SEQUENCE: 14

```
ggtgataagc ctagcccatt tggtcaggct gctgctggtg acaaaccgtc tccgttcggt      60
caggctgctg aaccgaaatc tgctgaaccg aaaccggctg aaccgaaaag caaagctgct     120
atcgctccgg ctaaagctgc tgctgctccg gctaaagctg ctaccgctcc ggcctcttct     180
atgccgtctg gtacctctga agaaggttct cgtggtggtt cttctatgcc ggccgaattc     240
tatgattcca ccgcccatgg taccccctagc accccgccg attcctccgc ccattccacc     300
ccatccaccc cagcctatga aaacaaaaa gccgccgaag ccaccaaagt agcagaagcc     360
gaaaaacaac gtgccgcaga agccaccaaa gtagccgaag ccgccctccc ccaagaagaa     420
caagaagatg tcggtccccg ccatgtagat ccagaccact ttcgctccac cacacaagat     480
gcctaccgcc cagttgaccc ctccgcctat aaacgtaagc ttaaatttgc ggaactgctg     540
gaacagcaga aaaacgcgca gtttccgggc aaagagctca ctagttaact cgag           594
```

<210> SEQ ID NO 15
<211> LENGTH: 195
<212> TYPE: PRT
<213> ORGANISM: Artificial Sequence
<220> FEATURE:
<223> OTHER INFORMATION: Made in a lab

<400> SEQUENCE: 15

```
Gly Asp Lys Pro Ser Pro Phe Gly Gln Ala Ala Ala Gly Asp Lys Pro
  1               5                  10                  15

Ser Pro Phe Gly Gln Ala Ala Glu Pro Lys Ser Ala Glu Pro Lys Pro
                 20                  25                  30

Ala Glu Pro Lys Ser Lys Ala Ala Ile Ala Pro Ala Lys Ala Ala Ala
             35                  40                  45

Ala Pro Ala Lys Ala Ala Thr Ala Pro Ala Ser Ser Met Pro Ser Gly
         50                  55                  60

Thr Ser Glu Glu Gly Ser Arg Gly Gly Ser Ser Met Pro Ala Glu Phe
 65                  70                  75                  80

Tyr Asp Ser Thr Ala His Gly Thr Pro Ser Thr Pro Ala Asp Ser Ser
                 85                  90                  95

Ala His Ser Thr Pro Ser Thr Pro Ala Tyr Glu Lys Gln Lys Ala Ala
            100                 105                 110

Glu Ala Thr Lys Val Ala Glu Ala Glu Lys Gln Arg Ala Ala Glu Ala
            115                 120                 125

Thr Lys Val Ala Glu Ala Ala Leu Pro Gln Glu Glu Gln Glu Asp Val
        130                 135                 140

Gly Pro Arg His Val Asp Pro Asp His Phe Arg Ser Thr Thr Gln Asp
145                 150                 155                 160

Ala Tyr Arg Pro Val Asp Pro Ser Ala Tyr Lys Arg Lys Leu Lys Phe
                165                 170                 175

Ala Glu Leu Leu Glu Gln Gln Lys Asn Ala Gln Phe Pro Gly Lys Glu
            180                 185                 190

Leu Thr Ser
        195
```

<210> SEQ ID NO 16
<211> LENGTH: 645

<212> TYPE: DNA
<213> ORGANISM: Artificial Sequence
<220> FEATURE:
<223> OTHER INFORMATION: Made in a lab

<400> SEQUENCE: 16

```
ggtgataagc ctagcccatt tggtcaggct gctgctggtg acaaaccgtc tccgttcggt      60
caggctgctg aaccgaaatc tgctgaaccg aaaccggctg aaccgaaaag caaagctgct     120
atcgctccgg ctaaagctgc tgctgctccg gctaaagctg ctaccgctcc ggcctcttct     180
atgccgtctg gtacctctga agaaggttct cgtggtggtt cttctatgcc ggccgaattc     240
tatgattcca ccgcccatgg tacccctagc accccgccg attcctccgc ccattccacc     300
ccatccaccc cagcctatga aaacaaaaa gccgccgaag ccaccaaagt agcagaagcc     360
gaaaaacaac gtgccgcaga agccaccaaa gtagccgaag ccgccctccc ccaagaagaa     420
caagaagatg tcggtccccg ccatgtagat ccagaccact ttcgctccac cacacaagat     480
gcctaccgcc cagttgaccc ctccgcctat aaacgtaagc ttaaatttgc ggaactgctg     540
gaacagcaga aaaacgcgca gtttccgggc aaagagctca aatttgcgga actgctggaa     600
cagcagaaaa acgcgcagtt tccgggcaaa gagctcacta gttaa                    645
```

<210> SEQ ID NO 17
<211> LENGTH: 210
<212> TYPE: PRT
<213> ORGANISM: Artificial Sequence
<220> FEATURE:
<223> OTHER INFORMATION: Made in a lab

<400> SEQUENCE: 17

```
Gly Asp Lys Pro Ser Pro Phe Gly Gln Ala Ala Gly Asp Lys Pro
 1               5                  10                  15

Ser Pro Phe Gly Gln Ala Ala Glu Pro Lys Ser Ala Glu Pro Lys Pro
            20                  25                  30

Ala Glu Pro Lys Ser Lys Ala Ala Ile Ala Pro Ala Lys Ala Ala
        35                  40                  45

Ala Pro Ala Lys Ala Ala Thr Ala Pro Ala Ser Ser Met Pro Ser Gly
    50                  55                  60

Thr Ser Glu Glu Gly Ser Arg Gly Gly Ser Ser Met Pro Ala Glu Phe
65                  70                  75                  80

Tyr Asp Ser Thr Ala His Gly Thr Pro Ser Thr Pro Ala Asp Ser Ser
                85                  90                  95

Ala His Ser Thr Pro Ser Thr Pro Ala Tyr Glu Lys Gln Lys Ala Ala
            100                 105                 110

Glu Ala Thr Lys Val Ala Glu Ala Glu Lys Gln Arg Ala Ala Glu Ala
        115                 120                 125

Thr Lys Val Ala Glu Ala Ala Leu Pro Gln Glu Glu Gln Glu Asp Val
    130                 135                 140

Gly Pro Arg His Val Asp Pro Asp His Phe Arg Ser Thr Thr Gln Asp
145                 150                 155                 160

Ala Tyr Arg Pro Val Asp Pro Ser Ala Tyr Lys Arg Lys Leu Lys Phe
                165                 170                 175

Ala Glu Leu Leu Glu Gln Gln Lys Asn Ala Gln Phe Pro Gly Lys Glu
            180                 185                 190

Leu Lys Phe Ala Glu Leu Leu Glu Gln Gln Lys Asn Ala Gln Phe Pro
        195                 200                 205

Gly Lys
```

<210> SEQ ID NO 18
<211> LENGTH: 855
<212> TYPE: DNA
<213> ORGANISM: Artificial Sequence
<220> FEATURE:
<223> OTHER INFORMATION: Made in a lab

<400> SEQUENCE: 18

```
ggtgataagc ctagcccatt tggtcaggct gctgctggtg acaaaccgtc tccgttcggt      60
caggctgctg aaccgaaatc tgctgaaccg aaaccggctg aaccgaaaag caaagctgct     120
atcgctccgg ctaaagctgc tgctgctccg gctaaagctg ctaccgctcc ggcctcttct     180
atgccgtctg gtacctctga agaaggttct cgtggtggtt cttctatgcc ggccgaattc     240
tatgattcca ccgcccatgg taccccctagc accccgccg attcctccgc ccattccacc     300
ccatccaccc cagcctatga aaacaaaaa gccgccgaag ccaccaaagt agcagaagcc     360
gaaaaacaac gtgccgcaga agccaccaaa gtagccgaag ccgccctccc ccaagaagaa     420
caagaagatg tcggtccccg ccatgtagat ccagaccact ttcgctccac cacacaagat     480
gcctaccgcc cagttgaccc ctccgcctat aaacgtaagc ttaaatttgc ggaactgctg     540
gaacagcaga aaaacgcgca gtttccgggc aaagagctca aatttgcgga actgctggaa     600
cagcagaaaa acgcgcagtt tccgggcaaa gagctcacta gtatggaaca ggaacgccgc     660
cagctgctgg aaaaagatcc gcgccgcaac gcgaaagaaa ttgcggcgct ggaagaaagc     720
atgaacgcgc gcgcgcagga actggcgcgc gaaaaaaaac tggcggatcg cgcgtttctg     780
gatcagaaac cggaacgcgt cccgctggcg gatgtcccgc tggatgatga tagcgatttt     840
gtcgcgtaac tcgag                                                       855
```

<210> SEQ ID NO 19
<211> LENGTH: 282
<212> TYPE: PRT
<213> ORGANISM: Artificial Sequence
<220> FEATURE:
<223> OTHER INFORMATION: Made in a lab

<400> SEQUENCE: 19

```
Gly Asp Lys Pro Ser Pro Phe Gly Gln Ala Ala Ala Gly Asp Lys Pro
  1               5                  10                  15
Ser Pro Phe Gly Gln Ala Ala Glu Pro Lys Ser Ala Glu Pro Lys Pro
             20                  25                  30
Ala Glu Pro Lys Ser Lys Ala Ala Ile Ala Pro Ala Lys Ala Ala Ala
         35                  40                  45
Ala Pro Ala Lys Ala Ala Thr Ala Pro Ala Ser Ser Met Pro Ser Gly
     50                  55                  60
Thr Ser Glu Glu Gly Ser Arg Gly Gly Ser Ser Met Pro Ala Glu Phe
 65                  70                  75                  80
Tyr Asp Ser Thr Ala His Gly Thr Pro Ser Thr Pro Ala Asp Ser Ser
                 85                  90                  95
Ala His Ser Thr Pro Ser Thr Pro Ala Tyr Glu Lys Gln Lys Ala Ala
            100                 105                 110
Glu Ala Thr Lys Val Ala Glu Ala Glu Lys Gln Arg Ala Ala Glu Ala
        115                 120                 125
Thr Lys Val Ala Glu Ala Ala Leu Pro Gln Glu Glu Gln Glu Asp Val
    130                 135                 140
```

```
Gly Pro Arg His Val Asp Pro Asp His Phe Arg Ser Thr Thr Gln Asp
145                 150                 155                 160

Ala Tyr Arg Pro Val Asp Pro Ser Ala Tyr Lys Arg Lys Leu Lys Phe
                165                 170                 175

Ala Glu Leu Leu Glu Gln Gln Lys Asn Ala Gln Phe Pro Gly Lys Glu
            180                 185                 190

Leu Lys Phe Ala Glu Leu Leu Glu Gln Gln Lys Asn Ala Gln Phe Pro
        195                 200                 205

Gly Lys Glu Leu Thr Ser Met Glu Gln Glu Arg Arg Gln Leu Leu Glu
    210                 215                 220

Lys Asp Pro Arg Arg Asn Ala Lys Glu Ile Ala Ala Leu Glu Glu Ser
225                 230                 235                 240

Met Asn Ala Arg Ala Gln Glu Leu Ala Arg Glu Lys Lys Leu Ala Asp
                245                 250                 255

Arg Ala Phe Leu Asp Gln Lys Pro Glu Arg Val Pro Leu Ala Asp Val
                260                 265                 270

Pro Leu Asp Asp Asp Ser Asp Phe Val Ala
                275                 280

<210> SEQ ID NO 20
<211> LENGTH: 270
<212> TYPE: PRT
<213> ORGANISM: Artificial Sequence
<220> FEATURE:
<223> OTHER INFORMATION: Made in a lab

<400> SEQUENCE: 20

Gly Asp Lys Pro Ser Pro Phe Gly Gln Ala Ala Ala Gly Asp Lys Pro
1               5                   10                  15

Ser Pro Phe Gly Gln Ala Ala Glu Pro Lys Ser Ala Glu Pro Lys Pro
            20                  25                  30

Ala Glu Pro Lys Ser Lys Ala Ala Ile Ala Pro Ala Lys Ala Ala Ala
        35                  40                  45

Ala Pro Ala Lys Ala Ala Thr Ala Pro Ala Ser Ser Met Pro Ser Gly
    50                  55                  60

Thr Ser Glu Glu Gly Ser Arg Gly Gly Ser Ser Met Pro Ala Glu Phe
65                  70                  75                  80

Tyr Asp Ser Thr Ala His Gly Thr Pro Ser Thr Pro Ala Asp Ser Ser
                85                  90                  95

Ala His Ser Thr Pro Ser Thr Pro Ala Tyr Glu Lys Gln Lys Ala Ala
            100                 105                 110

Glu Ala Thr Lys Val Ala Glu Ala Glu Lys Gln Arg Ala Ala Glu Ala
        115                 120                 125

Thr Lys Val Ala Glu Ala Ala Leu Pro Gln Glu Gln Gln Glu Asp Val
    130                 135                 140

Gly Pro Arg His Val Asp Pro Asp His Phe Arg Ser Thr Thr Gln Asp
145                 150                 155                 160

Ala Tyr Arg Pro Val Asp Pro Ser Ala Tyr Lys Arg Lys Leu Lys Phe
                165                 170                 175

Ala Glu Leu Leu Glu Gln Gln Lys Asn Ala Gln Phe Pro Gly Lys Glu
            180                 185                 190

Leu Lys Phe Ala Glu Leu Leu Glu Gln Gln Lys Asn Ala Gln Phe Pro
        195                 200                 205

Gly Lys Arg Ala Gln Glu Leu Ala Arg Glu Lys Lys Leu Ala Asp Arg
    210                 215                 220
```

```
Ala Phe Leu Asp Gln Lys Pro Glu Arg Val Pro Leu Ala Asp Val Pro
225                 230                 235                 240

Leu Asp Asp Asp Ser Asp Phe Val Ala Met Glu Gln Glu Arg Arg Gln
                245                 250                 255

Leu Leu Glu Lys Asp Pro Arg Arg Asn Ala Lys Glu Ile Ala
            260                 265                 270

<210> SEQ ID NO 21
<211> LENGTH: 762
<212> TYPE: DNA
<213> ORGANISM: Artificial Sequence
<220> FEATURE:
<223> OTHER INFORMATION: Made in a lab

<400> SEQUENCE: 21
ggtgataagc ctagcccatt tggtcaggct gctgctggtg acaaaccgtc tccgttcggt      60
caggctgctg aaccgaaatc tgctgaaccg aaaccggctg aaccgaaaag caaagctgct     120
atcgctccgg ctaaagctgc tgctgctccg gctaaagctg ctaccgctcc ggcctcttct     180
atgccgtctg gtacctctga gaaggttct cgtggtggtt cttctatgcc ggccgaattc      240
tatgattcca ccgccatgg taccctagc accccgccg attcctccgc ccattccacc       300
ccatccaccc cagcctatga aaaacaaaaa gccgccgaag ccaccaaagt agcagaagcc     360
gaaaaacaac gtgccgcaga agccaccaaa gtagccgaag ccgccctccc ccaagaagaa     420
caagaagatg tcggtccccg ccatgtagat ccagaccact ttcgctccac cacacaagat     480
gcctaccgcc cagttgaccc ctccgcctat aaacgtaagc ttaaatttgc ggaactgctg     540
gaacagcaga aaacgcgca gtttccgggc aaagagctca atttgcgga actgctggaa      600 cagcagaaaa acgcgcagtt tccgggcaaa gagctcacta gtcgcgcgca ggaactggcg     660
cgcgaaaaaa aactggcgga tcgcgcgttt ctggatcaga accggaacg cgtcccgctg      720 gcggatgtcc cgctggatga tgatagcgat tttgtcgcgt aa                       762

<210> SEQ ID NO 22
<211> LENGTH: 253
<212> TYPE: PRT
<213> ORGANISM: Artificial Sequence
<220> FEATURE:
<223> OTHER INFORMATION: Made in a lab

<400> SEQUENCE: 22

Gly Asp Lys Pro Ser Pro Phe Gly Gln Ala Ala Ala Gly Asp Lys Pro
1               5                   10                  15

Ser Pro Phe Gly Gln Ala Ala Glu Pro Lys Ser Ala Glu Pro Lys Pro
            20                  25                  30

Ala Glu Pro Lys Ser Lys Ala Ala Ile Ala Pro Ala Lys Ala Ala Ala
        35                  40                  45

Ala Pro Ala Lys Ala Ala Thr Ala Pro Ala Ser Ser Met Pro Ser Gly
    50                  55                  60

Thr Ser Glu Glu Gly Ser Arg Gly Gly Ser Ser Met Pro Ala Glu Phe
65                  70                  75                  80

Tyr Asp Ser Thr Ala His Gly Thr Pro Ser Thr Pro Ala Asp Ser Ser
                85                  90                  95

Ala His Ser Thr Pro Ser Thr Pro Ala Tyr Glu Lys Gln Lys Ala Ala
            100                 105                 110

Glu Ala Thr Lys Val Ala Glu Ala Glu Lys Gln Arg Ala Ala Glu Ala
        115                 120                 125
```

-continued

Thr Lys Val Ala Glu Ala Ala Leu Pro Gln Glu Gln Glu Asp Val
        130                 135                 140

Gly Pro Arg His Val Asp Pro Asp His Phe Arg Ser Thr Thr Gln Asp
145                 150                 155                 160

Ala Tyr Arg Pro Val Asp Pro Ser Ala Tyr Lys Arg Lys Leu Lys Phe
                165                 170                 175

Ala Glu Leu Leu Glu Gln Gln Lys Asn Ala Gln Phe Pro Gly Lys Glu
            180                 185                 190

Leu Lys Phe Ala Glu Leu Leu Glu Gln Gln Lys Asn Ala Gln Phe Pro
        195                 200                 205

Gly Lys Glu Leu Thr Ser Arg Ala Gln Glu Leu Ala Arg Glu Lys Lys
        210                 215                 220

Leu Ala Asp Arg Ala Phe Leu Asp Gln Lys Pro Glu Arg Val Pro Leu
225                 230                 235                 240

Ala Asp Val Pro Leu Asp Asp Asp Ser Asp Phe Val Ala
                245                 250

<210> SEQ ID NO 23
<211> LENGTH: 447
<212> TYPE: DNA
<213> ORGANISM: T. Cruzi

<400> SEQUENCE: 23
atgggcagca gccatcatca tcatcatcac agcagcggcc tggtgccgcg cggcagccat      60
atggccgcag gcggagagct ggcggcaaca gcagctgcag tgcggggaca gtttgcatcg     120
tgtgcccgtg ggggaaggac gacatggcgc aggatgggct tctggaggct gagcttttca     180
ccccggtgga tgagagcctc tagtccagca gacgtgctga gcatgggggag aaggagctgt     240
gaccgccccg tattttggcc tcagagccag agtgcaccct gtcgaaggca aaaggggcg      300
aagtcgacac aatgcgactt gtccacgaag cgcttcttcc tcccatgctc tggcagaggc     360
gtgccgggag atactgcga acagttgcgc ttttgttgtt ggctgtggtg gcggggaggg      420
cggagggca gactcaactg aaagctt                                          447

<210> SEQ ID NO 24
<211> LENGTH: 146
<212> TYPE: PRT
<213> ORGANISM: T. Cruzi

<400> SEQUENCE: 24

Met Gly Ser Ser His His His His His His Ser Ser Gly Leu Val Pro
 1               5                   10                  15

Arg Gly Ser His Met Ala Ala Gly Gly Glu Leu Ala Ala Thr Ala Ala
                20                  25                  30

Ala Val Arg Gly Gln Phe Ala Ser Cys Ala Arg Gly Gly Arg Thr Thr
            35                  40                  45

Trp Arg Arg Met Gly Phe Trp Arg Leu Ser Phe Ser Pro Arg Trp Met
        50                  55                  60

Arg Ala Ser Ser Pro Ala Asp Val Leu Ser Met Gly Arg Arg Ser Cys
65                  70                  75                  80

Asp Arg Pro Val Phe Trp Pro Gln Ser Gln Ser Ala Pro Cys Arg Arg
                85                  90                  95

Gln Lys Gly Ala Lys Ser Thr Gln Cys Asp Leu Ser Thr Lys Arg Phe
            100                 105                 110

Phe Leu Pro Cys Ser Gly Arg Gly Val Pro Gly Gly Tyr Cys Glu Gln
        115                 120                 125

Leu Arg Phe Cys Cys Trp Leu Trp Trp Arg Gly Gly Arg Arg Gly Arg
    130                 135                 140

Leu Asn
145

<210> SEQ ID NO 25
<211> LENGTH: 383
<212> TYPE: DNA
<213> ORGANISM: T. Cruzi

<400> SEQUENCE: 25
atgggcagca gccatcatca tcatcatcac agcagcggcc tggtgccgcg cggcagccat    60
atgcccaaaa agaccggtgg caaaagaag gggcaaagtt ctccggatgg ctctgagccg    120
cggaaacgaa agaacaacaa aaaggcgaca atggagccgc gggacgtgga tgagatgcag    180
aagctgcagg aacttttagg ggacgaggaa cagccgttgg gtgtctccaa gaaatcgcta    240
gagggcttat tgtcccttcg gcagccgcag gagttggcgg tgaggcttgc gcaatctctc    300 tcctcccctgc gcgcgcggct tgcggagttg gagttggaga ggcttaaccg tgggagcgag    360
gcgccggggc tgtcgaacat cgt    383

<210> SEQ ID NO 26
<211> LENGTH: 127
<212> TYPE: PRT
<213> ORGANISM: T. Cruzi

<400> SEQUENCE: 26

Met Gly Ser Ser His His His His His His Ser Ser Gly Leu Val Pro
  1               5                  10                  15

Arg Gly Ser His Met Pro Lys Lys Thr Gly Gly Lys Lys Gly Gln
             20                  25                  30

Ser Ser Pro Asp Gly Ser Glu Pro Arg Lys Arg Lys Asn Asn Lys Lys
         35                  40                  45

Ala Thr Met Glu Pro Arg Asp Val Asp Glu Met Gln Lys Leu Gln Glu
     50                  55                  60

Leu Leu Gly Asp Glu Glu Gln Pro Leu Gly Val Ser Lys Lys Ser Leu
 65                  70                  75                  80

Glu Gly Leu Leu Ser Leu Arg Gln Pro Gln Glu Leu Ala Val Arg Leu
                 85                  90                  95

Ala Gln Ser Leu Ser Ser Leu Arg Ala Arg Leu Ala Glu Leu Glu Leu
            100                 105                 110

Glu Arg Leu Asn Arg Gly Ser Glu Ala Pro Gly Leu Ser Asn Ile
        115                 120                 125

<210> SEQ ID NO 27
<211> LENGTH: 400
<212> TYPE: PRT
<213> ORGANISM: T. Cruzi

<400> SEQUENCE: 27

Met Pro Lys Lys Thr Gly Gly Lys Lys Gly Gln Ser Ser Pro Asp
  1               5                  10                  15

Gly Ser Glu Pro Arg Lys Arg Lys Asn Asn Lys Lys Ala Thr Met Glu
             20                  25                  30

Pro Arg Asp Val Asp Glu Met Gln Lys Leu Gln Glu Leu Leu Gly Asp
         35                  40                  45

Glu Glu Gln Pro Leu Gly Val Ser Lys Lys Ser Leu Glu Gly Leu Leu

```
                  50                  55                  60
Ser Leu Arg Gln Pro Gln Glu Leu Ala Val Arg Leu Ala Gln Ser Leu
 65                  70                  75                  80

Ser Ser Leu Arg Ala Arg Leu Ala Glu Leu Glu Leu Glu Arg Leu Asn
                 85                  90                  95

Arg Gly Ser Glu Ala Pro Gly Leu Ser Asn Ile Val Ala Arg Arg Ala
            100                 105                 110

Gln Glu Lys Ala Glu Lys Leu Glu Leu Glu Ile Gln Lys Thr Glu Arg
        115                 120                 125

Val Thr Arg Arg Leu Lys Ile Ile Ser Ser Leu Val Gly His Ile Ile
130                 135                 140

Arg Leu Arg Glu Lys Thr Leu Thr Glu Thr His Thr Ala Met Glu Ala
145                 150                 155                 160

Glu Val Gln Ser Leu Gln Glu Lys Ile Arg Val Asn Glu Glu Leu Ile
                165                 170                 175

Arg Glu Arg Phe Val Ser Arg Val Asn Met Leu His Arg Tyr Trp Leu
            180                 185                 190

Trp Arg Thr Leu Gln Glu Leu Gly Asp Gln Thr Val Gly Trp Thr Phe
        195                 200                 205

Glu Glu Glu Leu Ala Arg Gly Pro Arg Tyr Arg Thr Leu Gly Val Gln
210                 215                 220

Asn Asn Ile Val Ser Glu Thr Leu Glu Gln Gln Leu Ser Trp Leu Leu
225                 230                 235                 240

Val Phe Ala Glu Lys Glu Lys Ile Phe Arg Glu His Val Arg Arg Leu
                245                 250                 255

Glu Leu Leu Val Glu Glu Leu Thr Asp Ile Asn Asp Ala Leu Glu Glu
            260                 265                 270

Ala Leu Thr Cys Arg Val Cys Gly Leu Leu Phe Glu Asp Pro Val Leu
        275                 280                 285

Phe Trp Pro Cys Gly His Val Phe Cys Leu Val Cys Phe Asp Thr Leu
290                 295                 300

Ser Ile Ala Pro Ser Leu Phe Arg Cys Pro Thr Cys Gly Ser Met Gly
305                 310                 315                 320

Ser Glu Gly Tyr Val His Asn Leu Leu Ile Ala Glu Ser Val Ala Lys
                325                 330                 335

Trp Met Phe Lys Asp Ala Gly Tyr Gly Asp Ile His Gly Ala Leu Ser
            340                 345                 350

Leu Ile Arg Leu His Leu Ser Lys Phe Arg Lys Glu Val Ile Ser Ser
        355                 360                 365

Arg Val Ala Gln Leu His Gln Gln Leu Thr Glu Ala Arg Gln Lys Glu
370                 375                 380

Thr Lys Val Glu Glu Leu Ser Gln Met Asp Ile Thr Tyr Arg Asp Phe
385                 390                 395                 400

<210> SEQ ID NO 28
<211> LENGTH: 515
<212> TYPE: DNA
<213> ORGANISM: T. Cruzi

<400> SEQUENCE: 28
ccatgggcag cagccatcat catcatcatc acagcagcgg cctggtgccg cgcggcagcc      60
atatgtgcat tgctcttggc atcgtcgcgg aggatgatga ggcatggcga attgccagcg     120
aggctgtcgc tgcagaaaag gagcctgtct tcagcgggaa caacggccct tttgtagatg     180
```

```
tctggtttgg cgaacagaaa ctctttggcc tcgttcaacg cgttgctcca aacgacttta    240
ttcaggtcgc ccaggagtgt ggcgagaaga gcgatgacgc cgcagcgacg ttgcggatgc    300
gtgtgacgca caacgtctct tttgtccttc acctctcgtc ggtgccgcat gcgatgctgc    360
aggcacgggg agcgcccgag gacaagtttg tgaacttcat gcaacttgtc gtggattacg    420
cttcgctgct gcggcgcggg atgaaggatg agtttcttgg cgtcgatccc gagtccgatg    480
cggagtacat acgcttcacg ccccagtgaa agctt                                515

<210> SEQ ID NO 29
<211> LENGTH: 168
<212> TYPE: PRT
<213> ORGANISM: T. Cruzi

<400> SEQUENCE: 29

Met Gly Ser Ser His His His His His Ser Ser Gly Leu Val Pro
 1               5                  10                  15

Arg Gly Ser His Met Cys Ile Ala Leu Gly Ile Val Ala Glu Asp Asp
                20                  25                  30

Glu Ala Trp Arg Ile Ala Ser Glu Ala Val Ala Ala Glu Lys Glu Pro
            35                  40                  45

Val Phe Ser Gly Asn Asn Gly Pro Phe Val Asp Val Trp Phe Gly Glu
        50                  55                  60

Gln Lys Leu Phe Gly Leu Val Gln Arg Val Ala Pro Asn Asp Phe Ile
65                  70                  75                  80

Gln Val Ala Gln Glu Cys Gly Glu Lys Ser Asp Asp Ala Ala Ala Thr
                85                  90                  95

Leu Arg Met Arg Val Thr His Asn Val Ser Phe Val Leu His Leu Ser
            100                 105                 110

Ser Val Pro His Ala Met Leu Gln Ala Arg Gly Ala Pro Glu Asp Lys
        115                 120                 125

Phe Val Asn Phe Met Gln Leu Val Val Asp Tyr Ala Ser Leu Leu Arg
    130                 135                 140

Arg Gly Met Lys Asp Glu Phe Leu Gly Val Asp Pro Glu Ser Asp Ala
145                 150                 155                 160

Glu Tyr Ile Arg Phe Thr Pro Gln
                165

<210> SEQ ID NO 30
<211> LENGTH: 526
<212> TYPE: DNA
<213> ORGANISM: T. Cruzi

<400> SEQUENCE: 30
ccatgggcag cagccatcat catcatcatc acagcagcgg cctggtgccg cgcggcagcc     60
atatgtgttc caatacggga cccttgagga actcatcgca gcgtggaaga ccgatcgctg    120
tgtctgttgc caactcgtgt cttcgcgtag cggccacgca gaaagtttct aagccacctt    180
ctacagttca cccccggaat attggccggc aagcgactga ggactcgatg accaatgaac    240
tcaaaggcct tgctggagtc taccagcacc aacggagccc gatggggtct gcagtggagc    300
tggcttccaa caccgctctt cctgggaagg ttcacttgga attaatcgtt tctgttatgc    360
tcaaattcgt ttatcaggtg tgccagctgc atcgtcgtgg tacgcatact acggcacgca    420
tactggtgcg gacgaggcgt ccacagccaa agcagtctcc tcaatgccat tttctcagca    480
accttaccca cgatggaagg acagctgatt ggtcgatatg aagctt                   526
```

```
<210> SEQ ID NO 31
<211> LENGTH: 172
<212> TYPE: PRT
<213> ORGANISM: T. Cruzi

<400> SEQUENCE: 31

Met Gly Ser Ser His His His His His His Ser Ser Gly Leu Val Pro
1               5                   10                  15

Arg Gly Ser His Met Cys Ser Gln Tyr Gly Pro Leu Arg Asn Ser Ser
            20                  25                  30

Gln Arg Gly Arg Pro Ile Ala Val Ser Val Ala Asn Ser Cys Leu Arg
        35                  40                  45

Val Ala Ala Thr Gln Lys Val Ser Lys Pro Pro Ser Thr Val His Pro
    50                  55                  60

Arg Asn Ile Gly Arg Gln Ala Thr Glu Asp Ser Met Thr Asn Glu Leu
65                  70                  75                  80

Lys Gly Leu Ala Gly Val Tyr Gln His Gln Arg Ser Pro Met Gly Ser
                85                  90                  95

Ala Val Glu Leu Ala Ser Asn Thr Ala Leu Pro Gly Lys Val His Leu
            100                 105                 110

Glu Leu Ile Val Ser Val Met Leu Lys Phe Val Tyr Gln Val Cys Gln
        115                 120                 125

Leu His Arg Arg Gly Thr His Thr Thr Ala Arg Ile Leu Val Arg Thr
    130                 135                 140

Arg Arg Pro Gln Pro Lys Gln Ser Pro Gln Cys His Phe Leu Ser Asn
145                 150                 155                 160

Leu Thr His Asp Gly Arg Thr Ala Asp Trp Ser Ile
                165                 170
```

US 7,695,925 B2

COMPOSITIONS AND METHODS FOR THE DETECTION OF *TRYPANOSOMA CRUZI* INFECTION

REFERENCE TO RELATED APPLICATIONS

This application is the US national phase entry of International Patent Application No. PCT/US2006/042907, filed Nov. 2, 2006, which claims priority to U.S. Provisional Patent Application No. 60/733,119, filed Nov. 3, 2005.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. 2 R 44AIO52683-02 awarded by the National Institutes of Health.

FIELD OF THE INVENTION

The present invention relates generally to the diagnosis of *Trypanosoma cruzi* (*T. cruzi*) infection. More specifically, the invention relates to the use of *T. cruzi* antigenic polypeptides and fusion polypeptides in methods for screening individuals and blood supplies for *T. cruzi* infection.

BACKGROUND OF THE INVENTION

Protozoan parasites are a serious health threat in many areas of the world. *Trypanosoma cruzi* (*T. cruzi*) is one such parasite that infects millions of individuals. Ten to thirty percent of individuals infected with *T. cruzi* develop chronic symptomatic Chagas' disease, which may in turn lead to heart disease and a variety of immune system disorders. *T. cruzi* infection has long been a public health problem in Central and South America. It is estimated that 18 million people worldwide are chronically infected with *T. cruzi*, but available drug treatments lack efficacy and often cause serious side effects.

The most significant route of transmission in areas where the disease is endemic is through contact with an infected triatomid insect. However in other areas blood transfusions are the dominant means of transmission. Accordingly, in order to inhibit the transmission of *T. cruzi*, it is necessary to develop accurate methods for both diagnosing *T. cruzi* infection in individuals and for screening blood supplies. Blood bank screening is particularly important in South America, where 0.1%-62% of blood samples may be infected and where the parasite is frequently transmitted by blood transfusion. Due to high flow of immigrants to the US from many Central and South American countries where *T. cruzi* infection is endemic, the US blood supply is becoming at high risk for contamination from *T. cruzi* infected blood donors. While there are a few tests available for diagnosing infection in individuals, there is currently no FDA approved test available in the US for blood donor screening for *T. cruzi* infection.

The diagnosis of *T. cruzi* infection has been problematic, since accurate methods for detecting the parasite that are suitable for routine use have been unavailable. During the acute phase of infection, which may last for decades, the infection may remain quiescent and the host may be asymptomatic. As a result, serological tests for *T. cruzi* infection are the most reliable and the most commonly used form of diagnosis. Such diagnoses are complicated, however, by the complex life cycle of the parasite and the diverse immune responses of the host. The parasite passes through an epimastigote stage in the insect vector and two main stages in the mammalian host. One host stage is present in blood (the trypomastigote stage), while a second stage is intracellular (the amastigote stage). The multiple stages result in a diversity of antigens being presented by the parasite during infection. In addition, immune responses to protozoan infection are complex, involving both humoral and cell-mediated responses to the array of parasite antigens.

While detection of antibodies against parasite antigens is the most common and reliable method of diagnosing clinical and subclinical infections, current tests for *T. cruzi* infection are generally insensitive, lack specificity, and are not suitable for screening of blood supplies. Most serological tests use whole or lysed *T. cruzi* and require positive results on two of three tests, including complement fixation, indirect immunofluorescence, passive agglutination or ELISA, to accurately detect *T. cruzi* infection. The cost and difficulty of such tests has prevented the screening of blood or sera in many endemic areas.

U.S. Pat. Nos. 5,876,734 and 6,228,601 disclose compositions useful for diagnosing Chagas' disease that comprise a non-repetitive region of the *T. cruzi* protein TCR27, and fusion polypeptides including such regions. U.S. Pat. No. 6,419,933 discloses a fusion polypeptide referred to as TcF that contains the four antigenic *T. cruzi* peptides PEP-2, TcD, TcE and TcLo1.2, together with methods for the use of the fusion polypeptide in the detection of *T. cruzi* infection. While TcF is highly reactive with *T. cruzi*-infected sera from South America, it exhibits low activity, and is occasionally negative with, Central American sera. U.S. Pat. No. 6,458,922 discloses an assay for *T. cruzi* infection that employs compositions comprising at least six antigenic *T. cruzi* peptides selected from the group consisting of: SAPA, CRA, FRA, TcD, Tc24, Ag39 and MAP. Published US Patent Application No. US-2004/0132077-A1 discloses recombinant polypeptides and fusion polypeptides (referred to as FP3, FP4, FP5, FP6, FP7, FP8, FP9 and FP10) useful for diagnosing *T. cruzi* infection. The disclosed fusion polypeptides comprise modified versions of previously identified *T. cruzi* epitopes, including TC27, TCR39, SAPA and MAP.

SUMMARY OF THE INVENTION

The present invention provides compositions and methods for detecting *T. cruzi* infection in individuals and in biological samples, including blood supplies. The inventive compositions may be employed to detect *T. cruzi* infection in all geographical areas where Chagas' disease is present and with improved sensitivity compared to assays currently in use.

In one embodiment, the inventive compositions comprise the *T. cruzi* fusion polypeptide TcF (SEQ ID NO: 1), or a variant thereof, and at least one peptide selected from the group consisting of: SAPA (SEQ ID NO: 2); Pep30 (SEQ ID NO: 3); Pep36 (SEQ ID NO: 4); KMP-11 (SEQ ID NO: 5); Peptide 1 (SEQ ID NO: 6; also referred to as FRA; Lafaille et al., *Mol. Biochem. Parasitol.* 35:127-136, 1989); a modified version of peptide 1 (SEQ ID NO: 7); and variants thereof. The fusion polypeptide TcF and the at least one peptide may be present as individual components within the composition or may be linked to form a fusion polypeptide. In certain embodiments, the inventive compositions comprise the fusion polypeptide TcF in combination with the peptides Pep30, Pep36 and SAPA. Such compositions may, for example, include the fusion polypeptide of SEQ ID NO: 8 (referred to herein as ITC-6). In alternative embodiments, the inventive compositions include a fusion polypeptide comprising ITC-6 in combination with at least one repeat of the peptide KMP-11, and/or the peptide 1 sequences of SEQ ID NO: 6 or 7. The amino acid sequence of a representative fusion polypeptide comprising ITC-6 plus one repeat of KMP-11 (referred to as ITC7.1) is provided in SEQ ID NO: 15, with the amino acid sequence of a representative fusion polypeptide comprising ITC-6 plus two repeats of KMP-11 (referred to as ITC7.2) being provided in SEQ ID NO: 17. SEQ ID NO: 19 is the amino acid sequence of a representative fusion polypeptide comprising ITC7.2 plus peptide 1 (referred to as ITC8.2), with the corresponding DNA sequence being provided in SEQ ID NO: 18. The amino acid sequence of a shortened version of ITC8.2, referred to as ITC8.1, is provided in SEQ ID NO: 20. SEQ ID NO: 21 and 22 are the DNA and amino acid sequences, respectively, for a shortened version of ITC8.1.

Polynucleotides encoding the inventive fusion polypeptides, expression vectors comprising such polynucleotides, and host cells transformed or transfected with such expression vectors are also provided by the present invention.

As described in detail below, the inventors have determined that the inventive compositions may be employed to effectively detect T. cruzi infection in a biological sample. Accordingly, in one aspect, the present invention provides methods for detecting T. cruzi infection in a biological sample, comprising: (a) contacting the biological sample with a composition of the present invention; and (b) detecting in the biological sample the presence of antibodies that bind to an epitope present within the inventive composition, thereby detecting T. cruzi infection in the biological sample.

In a further aspect, diagnostic kits for detecting T. cruzi infection in a biological sample are provided, such kits comprising: (a) a composition of the present invention; and (b) a detection reagent.

The inventive compositions may also comprise at least one component selected from the group consisting of: physiologically acceptable carriers and immunostimulants. Methods for inducing protective immunity against Chagas' disease in a patient by administering such compositions are also encompassed by the present invention.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

BRIEF DESCRIPTION OF THE FIGURES

FIGS. 2A-C show the reactivity of TcF and ITC-6 with various sera as determined by ELISA. The RIPA status of the individual sera are shown in Table 1.

FIG. 3 shows the reactivity of the fusion polypeptides TcF, ITC-6, ITC7.1 and ITC7.2 on a panel of sera as determined by ELISA.

FIGS. 6A and 6B show the isolated DNA sequence and corresponding amino acid sequence, respectively, for TC5. The insert is shown in bold font, and the flanking sequence in non-bold font.

FIGS. 7A and 7B show the isolated DNA sequence and corresponding amino acid sequence, respectively, for TC48. The insert is shown in bold font, and the flanking sequence in non-bold font.

FIGS. 8A and 8B show the isolated DNA sequence and corresponding amino acid sequence, respectively, for TC60. The insert is shown in bold font, and the flanking sequence in non-bold font.

FIGS. 9A and 9B show the isolated DNA sequence and corresponding amino acid sequence, respectively, for TC70. The insert is shown in bold font, and the flanking sequence in non-bold font.

DETAILED DESCRIPTION OF THE INVENTION

Figure 1:
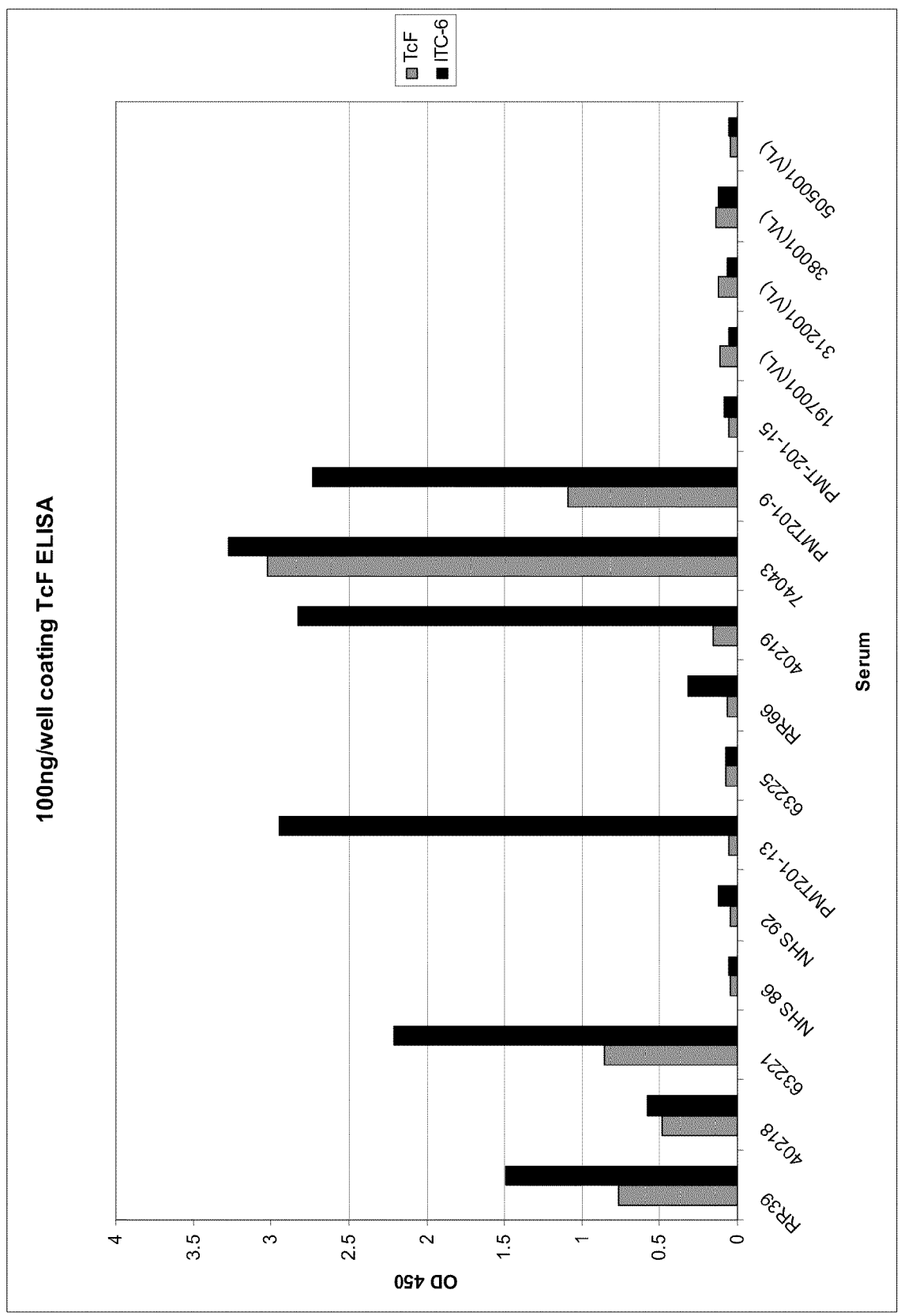
FIG. 1 shows the reactivity of the fusion polypeptides TcF and ITC-6 with T. cruzi-infected sera and control sera from non-infected individuals, as determined by ELISA.

As noted above, the present invention is generally directed to compositions and methods for detecting T. cruzi infection in individuals and for screening blood supplies for T. cruzi infection. The compositions of this invention generally comprise the known T. cruzi fusion polypeptide TcF (U.S. Pat. No. 6,419,933; SEQ ID NO: 1), or a variant thereof, and at least one antigenic T. cruzi epitope or polypeptide selected from the group consisting of: SAPA (SEQ ID NO: 2); Pep30 (SEQ ID NO: 3); Pep36 (SEQ ID NO: 4); KMP-11 (SEQ ID NO: 5); peptide 1 (SEQ ID NO: 6); modified peptide 1 (SEQ ID NO: 7); and variants thereof. The use of one or more additional epitopes from T. cruzi polypeptides, either prior to or in combination with one or more of the specific T. cruzi polypeptides disclosed herein, in order to enhance the sensitivity and specificity of detection is also contemplated by and encompassed within the present invention. The fusion polypeptide TcF and the at least one peptide may be present as individual components within the inventive composition or may be linked to form a fusion polypeptide. Fusion polypeptides comprising more than one repeat of the T. cruzi antigenic epitopes or polypeptides are also contemplated and encompassed by the present invention, as are fusion polypeptides in which the peptides are linked in an order which differs from those shown in the specific fusion polypeptide sequences provided herein.

In one embodiment, the inventive compositions include a fusion polypeptide comprising TcF, Pep30, Pep36 and SAPA, herein referred to as ITC-6 (SEQ ID NO: 8). In alternative embodiments, the inventive compositions include a fusion protein selected from the group consisting of SEQ ID NO: 15 (referred to as ITC7.1), SEQ ID NO: 17 (referred to as ITC7.2), SEQ ID NO: 19 (referred to as ITC8.2), and SEQ ID NO: 20 (referred to as ITC8.1). The DNA sequences for ITC-6, ITC7.1, ITC7.2 and ITC8.2 are provided in SEQ ID NO: 11, 14, 16 and 18, respectively.

As described in U.S. Pat. No. 6,419,933, the disclosure of which is hereby incorporated by reference, the fusion polypeptide TcF includes four antigenic epitopes, or peptides, referred to as PEP2, TcD, TcE and TcLo1.2. In an alternative embodiment, the inventive compositions may include these four individual peptides in place of the fusion protein TcF.

As used herein, the term "polypeptide" encompasses amino acid chains of any length, including full-length proteins, wherein amino acid residues are linked by covalent peptide bonds. Polypeptides disclosed herein may be naturally purified products, or may be produced partially or wholly using recombinant techniques. Such polypeptides may be glycosylated with mammalian or other eukaryotic carbohydrates or may be non-glycosylated. A polypeptide comprising an epitope may consist entirely of the epitope or may contain additional sequences. The additional sequences may be derived from the native antigen or may be heterologous, and such sequences may (but need not) be antigenic.

As used herein, a "fusion polypeptide" is a polypeptide in which epitopes of different antigens, or variants thereof, are joined, for example through a peptide linkage, into a single amino acid chain. The amino acid chain thus formed may be either linear or branched. The epitopes may be joined directly (i.e., with no intervening amino acids) or may be joined by way of a linker sequence that does not significantly alter the antigenic properties of the epitopes. The peptide epitopes may also be linked through non-peptide linkages, such as hetero- or homo-bifunctional agents that chemically or photochemically couple between specific functional groups on the peptide epitopes such as through amino, carboxyl, or sulfhydryl groups. Bifunctional agents which may be usefully employed in the combination polypeptides of the present invention are well known to those of skill in the art. Epitopes may also be linked by means of a complementary ligand/anti-ligand pair, such as avidin/biotin, with one or more epitopes being linked to a first member of the ligand/anti-ligand pair and then being bound to the complementary member of the ligand/anti-ligand pair either in solution or in solid phase. A fusion polypeptide may contain epitopes of one or more other *T. cruzi* antigens, linked to an epitope described herein.

A polynucleotide encoding a fusion protein of the present invention is constructed using known recombinant DNA techniques to assemble separate polynucleotides encoding the first and second polypeptides into an appropriate expression vector. The 3' end of a polynucleotide encoding a first polypeptide is ligated, with or without a peptide linker, to the 5' end of a polynucleotide encoding a second polypeptide so that the reading frames of the sequences are in phase to permit mRNA translation of the two polynucleotides into a single fusion protein that retains the biological activity of both the first and the second polypeptides.

As noted above, a peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference. The ligated polynucleotides encoding the fusion proteins are cloned into suitable expression systems using techniques known to those of ordinary skill in the art.

The present invention further provides polynucleotides that encode a polypeptide or fusion polypeptide of the present invention. Polynucleotides that comprise complements of such polynucleotide sequences, reverse complements of such polynucleotide sequences, or reverse sequences of such polynucleotide sequences, together with variants of such sequences, are also provided.

The definition of the terms "complement(s)," "reverse complement(s)," and "reverse sequence(s)," as used herein, is best illustrated by the following example. For the sequence 5' AGGACC 3', the complement, reverse complement, and reverse sequence are as follows:

```
complement              3' TCCTGG 5'
reverse complement      3' GGTCCT 5'
reverse sequence        5' CCAGGA 3'.
```

Preferably, sequences that are complements of a specifically recited polynucleotide sequence are complementary over the entire length of the specific polynucleotide sequence.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

All of the polypeptides, fusion polypeptides and polynucleotides described herein are isolated and purified, as those terms are commonly used in the art. Preferably, the polypeptides, fusion polypeptides and polynucleotides are at least about 80% pure, more preferably at least about 90% pure, and most preferably at least about 99% pure.

The compositions and methods of the present invention also encompass variants of the above polypeptides, fusion polypeptides and polynucleotides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 75%, more preferably at least 80%, more preferably at least 85%, more preferably at least 90%, more preferably yet at least 95%, and most preferably, at least 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100. In addition to exhibiting the recited level of sequence identity, variant sequences of the present invention preferably exhibit a functionality that is substantially similar to the functionality of the specific sequences disclosed herein. Variant fusion polypeptide sequences thus preferably retain the antigenic and diagnostic properties of the fusion polypeptides disclosed herein. Preferably a variant polypeptide or fusion polypeptide sequence will generate at least 80%, more preferably at least 85%, more preferably at least 90%, more preferably yet at least 95% and most preferably 100% of the response generated by the specifically identified polypeptide or fusion polypeptide sequence in an antibody binding assay, such as an ELISA assay. Such variants may generally be identified by modifying one of the polypeptide or fusion polypeptide sequences disclosed herein, and evaluating the antigenic and/ or diagnostic properties of the modified polypeptide or fusion polypeptide using, for example, the representative procedures described herein. Suitable assays for evaluating reactivity with *T. cruzi*-infected sera, such as an enzyme linked immunosorbent assay (ELISA), are described in more detail below, and in Harlow and Lane, *Antibodies: A Laboratory Manual*, Cold Spring Harbor Laboratory, 1988.

Variant sequences generally differ from the specifically identified sequence only by conservative substitutions, deletions or modifications. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptide and polynucleotide sequences may be aligned, and percentages of identical nucleotides in a specified region may be determined against another polynucleotide, using computer algorithms that are publicly available. Two exemplary algorithms for aligning and identifying the identity of polynucleotide sequences are the BLASTN and FASTA algorithms. The alignment and identity of polypeptide sequences may be examined using the BLASTP and algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444-2448, 1988; and in Pearson, *Methods in Enzymol.* 183:63-98, 1990. The FASTA software package is available from the University of Virginia, Charlottesville, Va. 22906-9025. The FASTA algorithm, set to the default parameters described in the documentation and distributed with the algorithm, may be used in the determination of polynucleotide variants. The readme files for FASTA and FASTX Version 2.0x that are distributed with the algorithms describe the use of the algorithms and describe the default parameters.

The BLASTN software is available on the NCBI anonymous FTP server and is available from the National Center for Biotechnology Information (NCBI), National Library of Medicine, Building 38A, Room 8N805, Bethesda, Md. 20894. The BLASTN algorithm Version 2.0.6 [Sep. 10, 1998] and Version 2.0.11 [Jan. 20, 2000] set to the default parameters described in the documentation and distributed with the algorithm, is preferred for use in the determination of variants according to the present invention. The use of the BLAST family of algorithms, including BLASTN, is described at NCBI's website and in the publication of Altschul, et al., "Gapped BLAST and PSI-BLAST: a new generation of protein database search programs," *Nucleic Acids Res.* 25:3389-3402, 1997.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity.

In general, *T. cruzi* polypeptides and fusion polypeptides, and polynucleotide sequences encoding such polypeptides and fusion polypeptides, may be prepared using any of a variety of procedures. For example, a *T. cruzi* cDNA or genomic DNA expression library may be screened with pools of sera from *T. cruzi*-infected individuals. Such screens may generally be performed using techniques well known to those of ordinary skill in the art, such as those described in Sambrook et al., *Molecular Cloning: A Laboratory Manual*, Cold Spring Harbor Laboratories, Cold Spring Harbor, N.Y., 1989. Briefly, the bacteriophage library may be plated and transferred to filters. The filters may then be incubated with serum and a detection reagent. In the context of this invention, a "detection reagent" is any compound capable of binding to the antibody-antigen complex, which may then be detected by any of a variety of means known to those of ordinary skill in the art. Typical detection reagents for screening purposes contain a "binding agent," such as Protein A, Protein G, IgG or a lectin, coupled to a reporter group. Preferred reporter groups include, but are not limited to, enzymes, substrates, cofactors, inhibitors, dyes, radionuclides, luminescent groups, fluorescent groups and biotin. More preferably, the reporter group is horseradish peroxidase (HRP), which may be detected by incubation with a substrate such as tetramethylbenzidine (TMB) or 2,2'-azino-di-3-ethylbenzthiazoline sulfonic acid. Plaques containing cDNAs that express a protein that binds to an antibody in the serum may be isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y., 1989.

Alternatively, polynucleotides encoding the fusion polypeptides disclosed herein may be amplified from *T. cruzi* genomic DNA or cDNA via polymerase chain reaction (PCR). For this approach, sequence-specific primers may be designed based on the polynucleotide sequence, and may be purchased or synthesized. An amplified portion of the DNA sequences may then be used to isolate the full length genomic or cDNA clones using well known techniques, such as those described in Sambrook et al., *Molecular Cloning: A Laboratory Manual*, Cold Spring Harbor Laboratories, Cold Spring Harbor, N.Y. (1989).

Polypeptides having fewer than about 100 amino acids, and generally fewer than about 50 amino acids, can be synthesized using, for example, the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied Biosystems Division, Foster City, Calif.

Polypeptides and fusion polypeptides may also be produced recombinantly by inserting a polynucleotide that encodes the fusion polypeptide into an expression vector and expressing the antigen in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, mycobacteria, insect, yeast or a mammalian cell line such as COS or CHO. The polynucleotides expressed in this manner may encode naturally occurring antigens, portions of naturally occurring antigens, or other variants thereof.

Expressed polypeptides and fusion polypeptides are generally isolated in substantially pure form. Preferably, the polypeptides and fusion polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

The present invention further provides methods for detecting *T. cruzi* infection in individuals and blood supplies. *T. cruzi* infection may be detected in any biological sample that contains antibodies. Preferably, the sample is blood, serum, plasma, saliva, cerebrospinal fluid or urine. More preferably, the sample is a blood or serum sample obtained from a patient or a blood supply. Briefly, *T. cruzi* infection may be detected using any one or more of the polypeptides or fusion polypeptides described above, or variants thereof, to determine the presence or absence of antibodies to the polypeptide or fusion polypeptide in the sample, relative to a predetermined cut-off value.

There are a variety of assay formats known to those of ordinary skill in the art for using purified antigen to detect antibodies in a sample. See, e.g., Harlow and Lane, *Antibodies: A Laboratory Manual*, Cold Spring Harbor Laboratory, 1988. In a preferred embodiment, the assay involves the use of polypeptide or fusion polypeptide immobilized on a solid support to bind to and remove the antibody from the sample. The bound antibody may then be detected using a detection reagent that binds to the antibody/fusion polypeptide complex and contains a detectable reporter group. Suitable detection reagents include antibodies that bind to the antibody/fusion polypeptide complex and free polypeptide labeled with a reporter group (e.g., in a semi-competitive assay). Alternatively, a competitive assay may be utilized, in which an antibody that binds to the fusion polypeptide is labeled with a reporter group and allowed to bind to the immobilized antigen after incubation of the antigen with the sample. The extent to which components of the sample inhibit the binding of the labeled antibody to the fusion polypeptide is indicative of the reactivity of the sample with the immobilized fusion polypeptide.

The solid support may be any solid material known to those of ordinary skill in the art to which the fusion polypeptide may be attached. For example, the solid support may be a test well in a microtiter plate, or a nitrocellulose or other suitable membrane. Alternatively, the support may be a bead or disc, formed of glass, fiberglass, latex or a plastic material such as polystyrene or polyvinylchloride. The support may also be a magnetic particle or a fiber optic sensor, such as those disclosed, for example, in U.S. Pat. No. 5,359,681.

The fusion polypeptide may be bound to the solid support using a variety of techniques known to those in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of fusion polypeptide ranging from about 10 ng to about 1 µg, and preferably about 100 ng, is sufficient to bind an adequate amount of antigen. Nitrocellulose will bind approximately 100 µg of protein per $cm^3$.

Covalent attachment of the polypeptide or fusion polypeptide to a solid support may generally be achieved by first reacting the support with a bifunctional reagent that will react with both the support and a functional group, such as a hydroxyl or amino group, on the fusion polypeptide. For example, the fusion polypeptide may be bound to supports having an appropriate polymer coating using benzoquinone or by condensation of an aldehyde group on the support with an amine and an active hydrogen on the fusion polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a polypeptide or fusion polypeptide that has been immobilized on a solid support, commonly the well of a microtiter plate, with the sample, such that antibodies to the polypeptide or fusion polypeptide within the sample are allowed to bind to the immobilized polypeptide or fusion polypeptide. Unbound sample is then removed from the immobilized polypeptide or fusion polypeptide and a detection reagent capable of binding to the immobilized antibody-polypeptide complex is added. The amount of detection reagent that remains bound to the solid support is then determined using a method appropriate for the specific detection reagent.

Once the polypeptide or fusion polypeptide is immobilized on the support, the remaining protein binding sites on the support are typically blocked using any suitable blocking agent known to those of ordinary skill in the art, such as bovine serum albumin or Tween 20™ (Sigma Chemical Co., St. Louis, Mo.). The immobilized polypeptide or fusion polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of *T. cruzi* antibody within a *T. cruzi*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *T. cruzi* antibodies in the sample, the signal detected from the reporter group that remains bound to the solid support is generally compared to a signal that corresponds to a predetermined cut-off value. This cut-off value is preferably the average mean signal obtained when the immobilized antigen is incubated with samples from an uninfected patient. In general, a sample generating a signal that is three standard deviations above the mean is considered positive for *T. cruzi* antibodies and *T. cruzi* infection. In an alternate preferred embodiment, the cut-off value is determined using a Receiver Operator Curve, according to the method of Sackett et al., *Clinical Epidemiology: A Basic Science for Clinical Medicine*, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for *T. cruzi* infection.

In a related embodiment, the assay is performed in a flow-through or strip test format, wherein the polypeptide or fusion polypeptide is immobilized on a membrane such as nitrocellulose. In the flow-through test, antibodies within the sample bind to the immobilized polypeptide or fusion polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide or fusion polypeptide is bound is immersed in a solution containing the sample. The sample migrates along the membrane through a region containing detection reagent and to the area of immobilized polypeptide or fusion polypeptide. Concentration of detection reagent at the polypeptide or fusion polypeptide indicates the presence of *T. cruzi* antibodies in the sample. Such tests can typically be performed with a very small amount (e.g., one drop) of patient serum or blood.

In yet another aspect of this invention, methods are provided for detecting *T. cruzi* in a biological sample using monospecific antibodies (which may be polyclonal or monoclonal) to one or more *T. cruzi* polypeptides or fusion polypeptides. Antibodies to purified or synthesized polypeptides may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Monospecific antibodies to epitopes of one or more of the polypeptides or fusion polypeptides described herein may be used to detect *T. cruzi* infection in a biological sample using any of a variety of immunoassays, which may be direct or competitive. Suitable biological samples for use in this aspect of the present invention are as described above. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of *T. cruzi* in the sample. To determine the presence or absence of *T. cruzi* infection, the signal detected from the reporter group that remains bound to the solid support is generally compared to a signal that corresponds to a predetermined cut-off value. Such cut-off values may generally be determined as described above. Any of the reporter groups discussed above in the context of ELISAs may be used to label the monospecific antibodies, and binding may be detected by any of a variety of techniques appropriate for the reporter group employed. Other formats for using monospecific antibodies to detect *T. cruzi* in a sample will be apparent to those of ordinary skill in the art, and the above formats is provided solely for exemplary purposes.

In another aspect of this invention, compositions are provided for the prevention or treatment of *T. cruzi* infection, and complications thereof, in a mammal. Such compositions generally comprise one or more fusion polypeptides disclosed herein, together with at least one component selected from the group consisting of: physiologically acceptable carriers and immunostimulants.

Routes and frequency of administration and fusion polypeptide doses will vary from individual to individual and may parallel those currently being used in immunization against other protozoan infections. In general, the compositions may be administered by injection (e.g., intracutaneous, intramuscular, intravenous or subcutaneous), intranasally (e.g., by aspiration), transdermally, orally or by transcutaneous patch as described, for example, in U.S. Pat. Nos. 5,910,306 and 5,980,898, the disclosures of which are hereby incorporated by reference. Between 1 and 4 doses may be administered for a 2-6 week period. Preferably, two doses are administered, with the second dose 2-4 weeks later than the first. A suitable dose is an amount of fusion polypeptide that is effective to raise antibodies in a treated mammal that are sufficient to protect the mammal from *T. cruzi* infection for a period of time. In general, the amount of fusion polypeptide present in a dose ranges from about 1 pg to about 100 mg per kg of host, typically from about 10 pg to about 1 mg, and preferably from about 100 pg to about 1 μg. Suitable dose sizes will vary with the size of the animal, but will typically range from about 0.01 mL to about 5 mL for 10-60 kg animal.

While any suitable carrier known to those of ordinary skill in the art may be employed in the compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of immunostimulants may be employed in the compositions of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A and quil A.

The following Examples are offered by way of illustration and not by way of limitation.

EXAMPLE 1

Design and Preparation of a Multi-Epitope Fusion Polypeptide

Serological expression studies employing *T. cruzi*-infected sera from Mexico and Central America that show little or no reactivity with the *T. cruzi* fusion protein TcF (SEQ ID NO: 1) were carried out to identify known *T. cruzi* antigens that will complement TcF with the goal of achieving high sensitivity and specificity. TcF (SEQ ID NO: 1), SAPA (SEQ ID NO: 2), Pep30 (SEQ ID NO: 3) and Pep36 (SEQ ID NO: 4) were found to have very good specificity and to complement each other in samples where TcF reactivity is low or zero.

Following these studies, a fusion polypeptide containing the TcF, Pep30, Pep36 and SAPA sequences was prepared in two steps.

In step one, SAPA, Pep30 and Pep36 were fused together with EcoR1 and Xho1 restriction sites to provide the polypeptide sequence of SEQ ID NO: 9 (referred to as SAPA3036; DNA sequence for *E. coli* expression provided in SEQ ID NO: 10) and cloned into a pUC related vector using standard techniques. In step two, SAPA3036 was digested with EcoR1 and Xho1, and subcloned into the 3' end of TcF (SEQ ID NO: 1). The amino acid sequence of the resulting fusion polypeptide (referred to as ITC-6) is provided in SEQ ID NO: 8, with the corresponding DNA sequence being provided in SEQ ID NO: 11. After sequence verification, expression was carried out in the Rosetta™ pLysS *E. coli* strain (Novagen, Madison, Wis.). The ITC-6 fusion polypeptide has sufficient flexibility at the DNA level for insertion of other antigenic epitopes, such as the KMP-11c *T. cruzi* specific sequence (SEQ ID NO: 5; Thomas et al., *Clin. Exp. Immunol.* 123:465-471, 2001), the Peptide 1 sequence (SEQ ID NO: 6) and the modified Peptide 1 sequence (SEQ ID NO: 7).

Oligonucleotides (SEQ ID NO: 12 and 13) were designed to PCR the SAPA3036 fusion protein for cloning directly into the pET28 vector in order to check expression and viability without the TcF component. The resulting PCR product was digested with Nde1 and Xho1 prior to cloning into pET28. There was no problem with expression of SAPA3036 without TcF.

It is envisioned that the order of the peptides in the recombinant fusion polypeptide ITC-6 could be altered without significantly changing the activity of the polypeptide. Also, the inclusion of a Gly-Cys-Gly linkage between the peptides may enhance solid phase binding without significantly affecting the activity of the polypeptide.

EXAMPLE 2

Detection of *T. cruzi* Infection in Sera Using ITC7.1 and ITC 7.2

The reactivity of sera from *T. cruzi*-infected individuals and control sera from non-infected individuals against the fusion polypeptides TcF and ITC-6 was determined by ELISA using the procedure described above. The results of this study are shown in FIG. 1. The *T. cruzi*-infected sera RR39, 40218, 63221, PMT201-13, RR66, 40219, 74043 and PMT201-9 had all been shown to be positive for *T. cruzi* by radio immunoprecipitation assay (RIPA). The serum 63225 is consensus positive, with the RIPA status being equivocal. NHS86, NHS92 and PMT201-15 are all normal sera. The 197001, 312001, 38001 and 505001 sera are all from individuals infected with visceral leishmaniasis (VL). The sera were assayed at 1/100 final dilution. Goat anti-human IgG-HRP was used for detection followed by the TMB substrate. As can be seen from FIG. 1, ITC-6 is capable of recognizing sera that are negative or low with TcF.

In subsequent studies, the reactivities of 56 sera (American Red Cross, 42; BBI 14) from the US, Central and South America previously determined to the positive by RIPA, and four endemic control sera from Mexico and Central American countries were tested against the recombinants TcF and ITC-6 by ELISA. The RIPA status of the individual sera are shown in Table 1 below. The coating concentration was 100 ng per well. All sera were tested at 1/100 final dilution. Following incubation, assays were developed using anti-human IgG-HRP and TMB substrate.

The results of these studies are shown in FIG. 2A-C. As predicted, ITC-6 detected *T. cruzi*-infected sera much better than TcF. All the endemic control sera were negative with TcF and ITC-6. Because of very low background and cross-reactivity with TcF and ITC-6, these can be used even at 200 ng per well. While there was 100% concordance with RIPA, with some sera (RR mix and Teragenix mix), the OD was low. These are mixes of several low titer sera and therefore represent dilutions of individual sera that were subsequently used in serological expression screening for additional antigens. In these cases, it is likely that use of other peptides, such as KMP-11 and peptide 1, in combination with ITC-6 will produce higher OD.

TABLE 1

RIPA status of different sera from North, South and Central America

| Serial Number | Serum ID | RIPA status |
|---|---|---|
| RR115 | *T. cruzi*(ARC) | Pos |
| RR99 | *T. cruzi*(ARC) | Pos |
| RR148 | *T. cruzi*(ARC) | Pos |
| RR131 | *T. cruzi*(ARC) | Pos |
| RR52 | *T. cruzi*(ARC) | Pos |
| RR167 | *T. cruzi*(ARC) | Pos |
| RR111 | *T. cruzi*(ARC) | Pos |
| RR71 | *T. cruzi*(ARC) | Pos |
| RR161 | *T. cruzi*(ARC) | Pos |
| RR78 | *T. cruzi*(ARC) | Pos |
| RR04 | *T. cruzi*(ARC) | Pos |
| RR38 | *T. cruzi*(ARC) | Pos |
| RR182 | *T. cruzi*(ARC) | Pos |
| RR102 | *T. cruzi*(ARC) | Pos |
| RR112 | *T. cruzi*(ARC) | Pos |
| RR164 | *T. cruzi*(ARC) | Pos |
| CRR94 | *T. cruzi*(ARC) | Pos |
| RR119 | *T. cruzi*(ARC) | Pos |
| RR86 | *T. cruzi*(ARC) | Pos |

TABLE 1-continued

RIPA status of different sera from North, South and Central America

| Serial Number | Serum ID | RIPA status |
|---|---|---|
| RR85 | *T. cruzi*(ARC) | Pos |
| RR34 | *T. cruzi*(ARC) | Pos |
| RR109 | *T. cruzi*(ARC) | Pos |
| RR73 | *T. cruzi*(ARC) | Pos |
| RR190 | *T. cruzi*(ARC) | Pos |
| CRR101 | *T. cruzi*(ARC) | Pos |
| RR171 | *T. cruzi*(ARC) | Pos |
| RR128 | *T. cruzi*(ARC) | Pos |
| RR105 | *T. cruzi*(ARC) | Pos |
| RR172 | *T. cruzi*(ARC) | Pos |
| RR174 | *T. cruzi*(ARC) | Pos |
| RR150 | *T. cruzi*(ARC) | Pos |
| RR181 | *T. cruzi*(ARC) | Pos |
| RR75 | *T. cruzi*(ARC) | Pos |
| RR57 | *T. cruzi*(ARC) | Pos |
| RR107 | *T. cruzi*(ARC) | Pos |
| RR39 | *T. cruzi*(ARC) | Pos |
| RR189 | *T. cruzi*(ARC) | Pos |
| RR163 | *T. cruzi*(ARC) | Pos |
| RR158 | *T. cruzi*(ARC) | Pos |
| RR157 | *T. cruzi*(ARC) | Pos |
| RR26 | *T. cruzi*(ARC) | Pos |
| RR94 | *T. cruzi*(ARC) | Pos |
| PMT201-1 | *T. cruzi*(BBI) | Pos |
| PMT201-2 | *T. cruzi*(BBI) | Pos |
| PMT201-3 | *T. cruzi*(BBI) | Pos |
| PMT201-4 | *T. cruz*(BBI) | Pos |
| PMT201-5 | *T. cruz*(BBI) | Pos |
| PMT201-6 | *T. cruzi*(BBI) | Pos |
| PMT201-7 | *T. cruzi*(BBI) | Pos |
| PMT201-8 | *T. cruzi*(BBI) | Pos |
| PMT201-9 | *T. cruz*(BBI) | Pos |
| PMT201-10 | *T. cruz*(BBI) | Pos |
| PMT201-11 | *T. cruzi*(BBI) | Pos |
| PMT201-12 | *T. cruz*(BBI) | Pos |
| PMT201-13 | *T. cruzi*(BBI) | Pos |
| PMT201-14 | *T. cruzi*(BBI) | Pos |
| PMT201-15 | Control serum (BBI) | Neg |
| NHS1 | Control serum | neg |
| NHS2 | Control serum | neg |
| NHS3 | Control serum | neg |
| | Low *T. cruzi* positive control | RR used in expression cloning |
| | Low *T. cruzi* positive control | Teragenix Mix *T. cruzi* used in expression cloning |

In FIG. 3, the reactivities of TcF and ITC-6 are compared with those of ITC-7.1 and 7.2 on a panel of sera. ITC-7.1 and 7.2 contain one and two repeats of the *T. cruzi* specific KMP-11 sequence. Assays were performed as described above. The reactivity of these sera with TcF, ITC-6, ITC-7.1 and 7.2 are compared in FIG. 3. The constructs ITC-7.1 and 7.2 showed comparable activity to ITC-6 with indications of possibly higher signal.

EXAMPLE 3

Detection of *T. cruzi* Infection in Sera Using ITC 7.2 and ITC 8.2

Recombinant protein for ITC8.2 (SEQ ID NO: 19) was expressed as described in Example 6 below. This protein was then used as the solid phase antigen in an ELISA assay and compared with ITC7.2 (SEQ ID NO: 17) which differs from ITC8.2 by not incorporating peptide 1 (SEQ ID NO: 6). Included in the group was a serum sample (sample no. 7190014) which was known to react with peptide 1 as well as other components of the multiepitope recombinant proteins.

Figure 4:
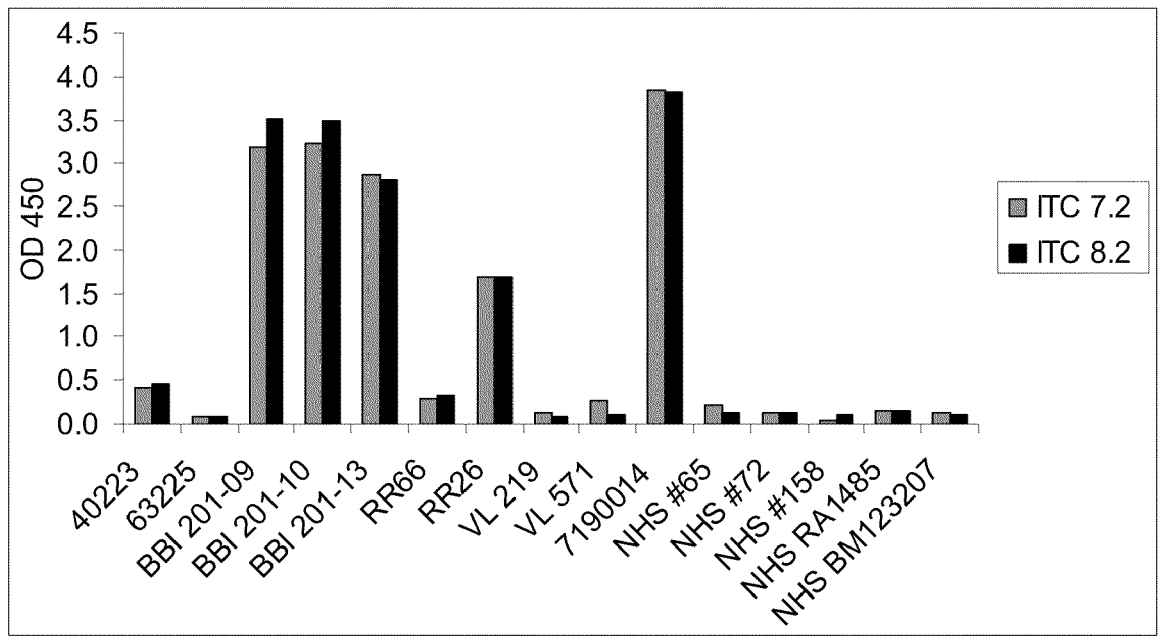
FIG. 4 shows the reactivity of the fusion polypeptides ITC7.2 and the shortened version of ITC8.2 provided in SEQ ID NO: 22 on a panel of sera as determined by ELISA.

The results of this study are shown in FIG. 4. As shown, comparable activity was seen with ITC8.2 and ITC7.2.

To ensure that peptide 1 is in fact functional in ITC8.1 (containing the short form of peptide 1 provided in SEQ ID NO: 7) and ITC8.2 (containing the full length peptide 1 provided in SEQ ID NO: 6), absorption studies were performed with a known peptide 1-reactive serum (sample no. 7190014, from the University of Chile) absorbed with beads coated with ITC7.2. Preparation of ITC7.2 coated beads treated with serum #7190014 was carried out as follows:

1) 100 ul of ITC-7.2 coated beads was centrifuged at 2000 rpm for 1 min.
2) The supernatant buffer was carefully removed and 1/10 diluted serum sample no. 7190014 in 10 mM Tris, pH8.0 was added to the ITC7.2 coated beads.
3) The mixture was gently rocked for approximately 1 hr at RT.
4) The mixture tube was centrifuged again at 200 rpm for 1 min.
5) The supernatant was further diluted to a final dilution of 1/20 and 1/100 with Sample Dilution Buffer (SDB) for IgG, 15 mM EDTA. Non-treated serum #7190014 was also directly diluted to 1/20 and 1/100 in serum dilution buffer.

Figure 5:
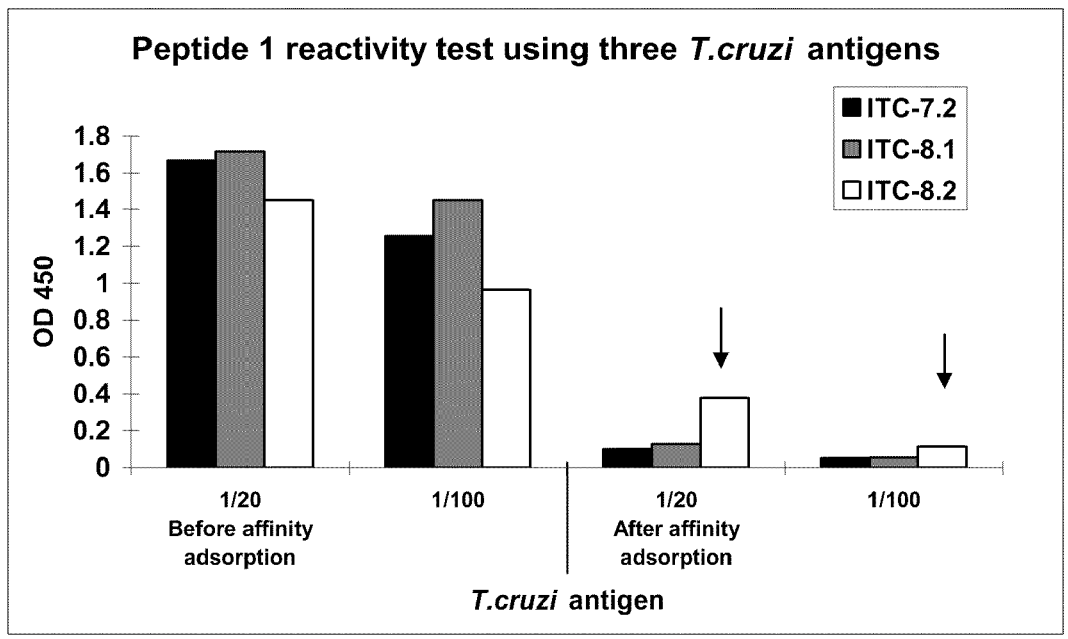
FIG. 5 shows the activity of non-absorbed and absorbed peptide 1-positive sera with ITC7.2, ITC8.1 and shortened ITC8.2 (SEQ ID NO: 22).

All samples were then tested in an ELISA with 100 µl per well of diluted sera being added to coated ITC7.2, shortened ITC8.1 (SEQ ID NO: 22) and ITC8.2 (SEQ ID NO: 19) microtiter strips (3.12 ng/well). *T. cruzi* ELISA was performed as outlined in Example 1. FIG. 5 shows the activity of non-absorbed and absorbed peptide 1-positive sera. Residual peptide 1 reactivity was observed only in ITC8.2, indicating that the shortened form of peptide 1 in shortened ITC8.1 was either unreactive or less active than the larger peptide 1 sequence present in ITC8.2.

EXAMPLE 4

Immunoblot with ITC Recombinant Proteins

Colloidal gold immunoblots were performed to determine if ITC-6 and ITC7.2 recombinant proteins detected *T. cruzi* positive sera that were low reactive or negative by the parent recombinant protein TcF. Also tested were 12 visceral leishmaniasis (VL) serum samples and sera from four normal donors. The data is shown in Table 2 below.

Briefly, the recombinant proteins were sprayed onto nitrocellulose, blocked with nonfat dried milk, washed in PBS Tween and cut into strips. Strips were incubated in serum at a 1/50 dilution for 15 minutes at 37° C. Strips were then washed in PBS Tween and further incubated for 6 min at ambient temperature with PA-gold (OD5) with ECL 10%. Blots were washed with PBS Tween 20 and observed for the presence or absence of a colored line.

The data (expressed as line intensity) indicate that both ITC6 and ITC7.2 greatly improve the detectability of *T. cruzi* positive sera as compared to TcF without jeopardizing specificity as indicated by no change in reactivity profile with both VL and normal donor sera.

TABLE 2

| Sample | Antigen | | |
|---|---|---|---|
| | ITC 6 | ITC 7.2 | TcF |
| 74042 | ++++ | ++++ | ± |
| 40222 | ++ | ++ | ± |
| 74044 | ++++ | ++++ | ± |
| 40119 | ++++ | ++++ | − |
| 40224 | ++ | ++ | − |
| 74040 | ++++ | ++++ | + |
| RR148 | − | − | − |
| RR174 | + | + | − |
| RR115 | ++ | ++ | ± |
| RR161 | +++ | +++ | − |
| RR131 | +++ | +++ | ± |
| VL474 | − | − | − |
| VL485 | − | − | − |
| VL487 | − | − | − |
| VL494 | − | − | − |
| VL507 | − | − | − |
| VL461 | − | − | − |
| VL453 | − | − | − |
| VL495 | − | − | − |
| VL494 | − | − | − |
| VL477 | − | − | − |
| VL488 | − | − | − |
| VL505 | − | − | − |
| NHS108 | − | − | − |
| NHS117 | − | − | − |
| NHS126 | − | − | − |
| NHS135 | − | − | − |

EXAMPLE 5

Rapid Test Data with ITC8.2

Rapid lateral flow immunoassays were performed using dipsticks prepared with ITC8.2 on the membrane and compared with radioimmunoprecipitation data, immunofluorescence, Lysate and ITC8.2 ELISA. The comparative data is shown in Table 3, below. Good correlation was seen between all assay formats.

TABLE 3

| | ELISA ITC8.2 | Chile | | | | |
|---|---|---|---|---|---|---|
| | 3.13 ng/well | IFAT titer | ELISA lysate | Peptide 1 ELISA | RIPA | Dipstick ITC8.2 |
| 7290140 | 2.988 | 320 | + | + | + | 4+ |
| 7290191 | 2.636 | 40 | + | + | + | 3+ |
| 7290192 | 2.785 | 40 | + | + | + | 4+ |
| 7290083 | 2.613 | 40 | + | − | + | 2+ |
| 7290062 | 1.417 | 40 | + | − | + | 1+ |
| 7190033 | 2.713 | 80 | + | + | + | 3+ |
| 7190024 | 2.677 | 40 | + | + | + | 3+ |
| 7190016 | 2.755 | 80 | + | + | + | 3+ |
| 7190120(733) | 0.055 | − | − | − | − | − |
| 7190026 | 1.966 | 40 | + | + | + | 2+ |
| 7290129 | 2.714 | 20 | + | + | + | 3+ |
| 7290189 | 1.856 | 20 | + | + | + | 1+ |
| 7290187 | 2.436 | 80 | + | + | + | 2+ |
| 7190012 | 2.732 | 160 | + | − | + | 4+ |
| 7190047 | 2.090 | 20 | + | + | + | 2+ |
| 7190052 | 0.060 | − | − | − | − | − |
| 7290183 | 0.574 | 40 | + | − | + | 2+ |
| 7290147 | 2.772 | + | + | + | + | 3+ |
| 7190045 | 2.576 | 20 | + | + | + | 4+ |
| 7190035 | 2.432 | 20 | + | + | + | 2+ |
| 7290144 | 2.412 | + | + | + | + | 4+ |
| 7190117(736) | 0.053 | − | − | − | − | +/− |
| 7190114 | 1.524 | 80 | + | | − | 1+ |
| 7190042 | 2.426 | 20 | + | + | + | 2+ |

TABLE 3-continued

| | ELISA ITC8.2 | Chile | | | | |
|---|---|---|---|---|---|---|
| | 3.13 ng/well | IFAT titer | ELISA lysate | Peptide 1 ELISA | RIPA | Dipstick ITC8.2 |
| 7290146 | 2.872 | 160 | + | + | + | 4+ |
| 7190113(755) | 0.064 | – | – | – | – | – |
| 7290145 | 2.063 | 20 | + | + | + | 2+ |
| 7190036 | 2.515 | 20 | + | + | + | 3+ |
| 7190119 | 0.044 | 80 | + | – | – | – |
| 7190116 | 0.087 | 320 | + | – | – | – |
| 7190115 | 0.110 | 20 | E | – | – | – |
| 7290190 | 2.472 | 160 | + | + | + | 4+ |
| 7190118 | 0.090 | 20 | E | – | – | +/– |
| 7190014 | 2.818 | 40 | + | + | + | 4+ |
| 823 | 0.051 | – | – | – | – | – |
| 838 | 0.051 | – | – | – | – | – |
| Panel #5 | 1.576 | ND | ND | ND | ND | ND |
| Panel #6 | 1.197 | ND | ND | ND | ND | ND |
| Panel #7 | 0.535 | ND | ND | ND | ND | ND |

EXAMPLE 6

Expression of ITC8.2 in SUMO Expression System and Improved Specificity

Two expression systems were compared to determine if improved expression of ITC8.2 was possible and also to improve upon specificity. *T. cruzi* positive and negative sera, and an antibody dilutional panel were run in the assay. Negative sera included problematic normal sera. The systems compared were the expression of a Hexahistidine tagged ITC8.2 in a pET17 vector versus an expression system using the SUMO expression system (no His Tag; Life Sensors, Inc., Malvern, Pa.) wherein the SUMO fragment was excised with the appropriate protease. The data, which is shown in Table 4, demonstrates the potential for improvement in specificity achieved when using the SUMO-derived recombinant versus preparing the hexahistidine ITC8.2 in a pET vector system.

TABLE 4

| | ELISA | ITC8.2 (His Tag) 20 min | ITC8.2 (SUMO) 20 min |
|---|---|---|---|
| 7290140 | P | 4+ | 4+ |
| 7290062 | P | 1+ | 2+ |
| 7190120(733) | N | – | – |
| 7190052 | N | – | – |
| 7290183 | P | 2+ | 2+ |
| 7190117(736) | N | +/– | – |
| 7190114 | P | 1+ | 2+ |
| 7190113(755) | N | – | – |
| 7190119 | N | – | – |
| 7190116 | N | – | – |
| 7190115 | N | – | – |
| 7190118 | N | +/–? | – |
| 823 | N | – | – |
| 838 | N | – | – |
| Chagas D#2 | P | 4+ | 4+ |
| Chagas D#4 | P | 3+ | 3+ |
| Chagas D#5 | P | 2.5+ | 1+ |
| Chagas D#6 | P | 1.5+ | + |
| BM123204 | | – | – |
| BM123207 | | +/– | – |
| BM123210 | | – | – |
| SeraCare#5 | | + | – |
| SeraCare#22 | | + | – |
| SeraCare#122 | | +/– | – |
| SeraCare#154 | | +/– | – |

EXAMPLE 7

Sequences Derived from Serological Expression Cloning

*T. cruzi* Library Preparation:

A genomic random shear expression library was constructed by sonicating genomic DNA from *Trypanosoma cruzi* CL strain. Sonication produced fragment sizes of 0.5-2.0 kb. Fifteen micrograms of sonicated DNA was treated with T4 polymerase (NEB) for 15 minutes at 12° C. followed by incubation for 20 minutes at 75° C. to produce blunt ended fragments. EcoRI adaptors were then ligated to the fragments and adaptors were phosphorylated with *E. coli* polynucleotide kinase. Fragments were next fractionated with a Sephacryl S400 column and finally ligated to a Lambda ZAP Express (Stratagene) vector. Ligated vector was packaged with Gigapack III Gold packaging extract (Stratagene).

Screening:

The amplified library was plated on LB agarose plates at a concentration of 20,000 plaque forming units (PFU) per 35 plates. After incubation at 42° C. for 4 hrs, nitrocellulose filters soaked in 10 mM IPTG were added and the plates were incubated at 37° C. overnight. Filters were removed and washed 3× with PBS containing 0.1% Tween 20 (PBST), blocked for 1 hr with 1% BSA in PBST, washed 3× with PBST, blocked another 1 hr with 1% Tween 20 in PBS, washed 3× with PBST and then incubated overnight at 4° C. in serum, patient pool #1 (RR mix) and/or pool #2 (Teragenix mix). Both patient serum pools were obtained from RIPA-confirmed low reactive *T. cruzi* sera. The following day, after washing 3× with PBST, filters were incubated in an alkaline phosphatase secondary antibody goat anti human Ig (IgG, IgA, IgM) for 1 hr at room temperature. Filters were finally washed 3× with PBST, 2× with AP buffer and developed with BCIP/NBT. Positive clones were purified using the same technique. Phagemid were excised, and resulting plasmid DNA was sequenced and searched against the *T. cruzi* databases.

Features and Outcome of Library Screening:

| | |
|---|---|
| Lambda vector: | Lambda Zap Express (Stratagene) |
| Plasmid vector: | pBK-CMV (kanamycin) |
| DNA: | Genomic *T. cruzi* |
| Library titer: | $2.5 \times 10^8$/ml (amplified) (total of 30 ml) |
| Insert size: | 0.5-2.0 Kbp (average = 1.1) |
| Screened: | 20,000 pfu per 35 plates |
| Serum: | Patient pool #1 and pool #2 (from normal donors) 1:200 dilution |
| Primary Picks: | 31 (Human Ig) from patient pool#1 (from 15 plates) |
| | 47 (Human Ig) from patient pool#2 (from 20 plates) |
| Purified Secondary: | 38 (weak-strong signal) |
| Submitted for Sequencing: | 12 |

TABLE 5

Hits from *T. cruzi* genomic library screening with pooled serum from infected patients

| Clone | Score | Blastn | Homology | Size (kDa) | GenBank |
|---|---|---|---|---|---|
| Tc-2 | 1816 | Tc00.1047053 509181.9 | dispersed gene family protein (DGF-1 pseudogene) | | M90534 *T. cruzi* protein 1 of DGF-1 |
| Tc-5 | 883 | Tc00.1047053 507757.10 | hypothetical protein | 14.2 | Novel |
| Tc-11 | 3025 | Tc00.1047053 509181.9 | dispersed gene family protein (DGF-1 pseudogene) | | M90534 *T. cruzi* protein 1 of DGF-1 |
| Tc-12 | 3784 | Tc00.1047053 509181.9 | dispersed gene family protein (DGF-1 pseudogene) | | M90534 *T. cruzi* protein 1 of DGF-1 |
| Tc-13 | 2765 | Tc00.1047053 509181.9 | dispersed gene family protein (DGF-1 pseudogene) | | M90534 *T. cruzi* protein 1 of DGF-1 |
| Tc-14 | 2330 | Tc00.1047053 509659.20 | dispersed gene family protein (DGF-1 pseudogene) | | M90534 *T. cruzi* protein 1 of DGF-1 |
| Tc-15 | 3277 | Tc00.1407053 511211.170 | Heat shock 70 | 73.2 | X58715 *T. cruzi* hsp 70 mRNA for 70 kDa HSP |
| Tc-19 | | | | | |
| Tc-25 | 2964 | Tc00.1407053 507713.30 | Heat shock 85 | 81 | M15346 *T. cruzi* 85 kDa heat shock protein |
| Tc-26 | 3175 | Tc00.1407053 510271.20 | dispersed gene family protein (DGF-1 pseudogene) | | |
| Tc-27 | 3362 | Tc00.1407053 503739.20 | trans-sialidase | | |
| Tc-31 | 3276 | | microtubule-associated protein | 125.5 | |

Additional sequences, referred to as Tc48, Tc60 and Tc70, were also identified. These sequences, plus Tc5, were of the most interest for further evaluation. The DNA sequences for Tc5, Tc48, Tc60 and Tc70 are provided in SEQ ID NO: 23, 25, 28 and 30, respectively, with the amino acid sequences for Tc5, Tc60 and Tc70 being provided in SEQ ID NO: 24, 29 and 31. The identified partial amino acid sequence of Tc48 is provided in SEQ ID NO: 26, with the corresponding full-length sequence obtained from the public database being provided in SEQ ID NO: 27.

From the foregoing, it will be appreciated that, although specific embodiments of the invention have been described herein for the purpose of illustration, various modifications may be made without deviating from the spirit and scope of the invention.

SEQ ID NO: 1-31 are set out in the attached Sequence Listing. The codes for polynucleotide and polypeptide sequences used in the attached Sequence Listing confirm to WIPO Standard ST.25 (1988), Appendix 2.

All references disclosed herein, including patent references and non-patent references, are hereby incorporated by reference in their entirety as if each was incorporated individually.

We claim:

1. A fusion polypeptide comprising an amino acid sequence selected from the group consisting of: SEQ ID NO: 8, 15, 17, 19, and 20.

2. A fusion polypeptide comprising an amino acid sequence selected from the group consisting of:
   (a) sequences having at least 90% identity to SEQ ID NO: 8, 15, 17, 19 or 20;
   (b) sequences having at least 95% identity to SEQ ID NO: 8, 15, 17, 19 or 20; and
   (c) sequences having at least 98% identity to SEQ ID NO: 8, 15, 17, 19 or 20.

3. A method for detecting T. cruzi infection in a biological sample, comprising:
   (a) contacting the biological sample with a fusion polypeptide of claim 1 to form an antibody-fusion polypeptide complex; and
   (b) contacting the antibody-fusion polypeptide complex with a detection reagent that binds to the complex, thereby detecting T. cruzi infection in the biological sample.

4. The method of claim 3, wherein the biological sample is selected from the group consisting of: blood, serum, plasma, saliva, cerebrospinal fluid and urine.

5. A diagnostic kit for detecting T. cruzi infection in a biological sample, comprising:
   (a) a fusion polypeptide of claim 1, and
   (b) a detection reagent.

6. The kit of claim 5, wherein the detection reagent comprises a reporter group.

7. The kit of claim 6, wherein the reporter group is selected from the group consisting of: enzymes, substrates, cofactors, inhibitors, dyes, radionuclides, luminescent groups, fluorescent groups, and biotin.

8. A composition comprising a fusion protein according to claim 1 and at least one component selected from the group consisting of: physiologically acceptable carriers and immunostimulants.

9. A method for detecting T. cruzi infection in a biological sample, comprising:
   (a) contacting the biological sample with a fusion polypeptide of SEQ ID NO: 19 to form an antibody-fusion polypeptide complex; and
   (b) contacting the antibody-fusion polypeptide complex with a detection reagent that binds to the complex, thereby detecting T. cruzi infection in the biological sample.

10. A diagnostic kit for detecting T. cruzi infection in a biological sample, comprising:
    (a) a fusion polypeptide of SEQ ID NO: 19; and
    (b) a detection reagent.

11. A composition comprising a fusion protein of SEQ ID NO: 19 and at least one component selected from the group consisting of: physiologically acceptable carriers and immunostimulants.

12. A method for detecting T. cruzi infection in a biological sample, comprising:

(a) contacting the biological sample with a fusion polypeptide of claim 2; and
(b) contacting the antibody-fusion polypeptide complex with a detection reagent that binds to the complex, thereby detecting *T. cruzi* infection in the biological sample.

13. The method of claim 12, wherein the biological sample is selected from the group consisting of: blood, serum, plasma, saliva, cerebrospinal fluid and urine.

14. A diagnostic kit for detecting *T. cruzi* infection in a biological sample, comprising:

(a) a fusion polypeptide of claim 2; and
(b) a detection reagent.

15. The kit of claim 14, wherein the detection reagent comprises a reporter group.

16. The kit of claim 15, wherein the reporter group is selected from the group consisting of: enzymes, substrates, cofactors, inhibitors, dyes, radionuclides, luminescent groups, fluorescent groups, and biotin.

* * * * *